US008259304B2

(12) United States Patent
Alphonse

(10) Patent No.: US 8,259,304 B2
(45) Date of Patent: Sep. 4, 2012

(54) BROADBAND DISCRETE SPECTRUM OPTICAL SOURCE

(76) Inventor: Gerard A Alphonse, Princeton, NJ (US)

(*) Notice: Subject to any disclaimer, the term of this patent is extended or adjusted under 35 U.S.C. 154(b) by 0 days.

(21) Appl. No.: 13/303,115

(22) Filed: Nov. 22, 2011

(65) Prior Publication Data

US 2012/0127472 A1 May 24, 2012

Related U.S. Application Data

(63) Continuation-in-part of application No. 13/111,047, filed on May 19, 2011.

(60) Provisional application No. 61/396,284, filed on May 26, 2010.

(51) Int. Cl.
*G01B 9/02* (2006.01)
*H01S 3/00* (2006.01)
*H01S 3/08* (2006.01)

(52) U.S. Cl. .......................... 356/479; 359/346; 372/92

(58) Field of Classification Search .................. 356/479, 356/497; 359/341.3, 344, 346; 372/6, 44.01, 372/92
See application file for complete search history.

(56) References Cited

U.S. PATENT DOCUMENTS

| | | | |
|---|---|---|---|
| 4,821,277 A | | 4/1989 | Alphonse et al. |
| 5,184,247 A | * | 2/1993 | Schimpe .................... 359/344 |
| 6,879,610 B2 | * | 4/2005 | Alphonse et al. .......... 372/49.01 |
| 6,937,780 B2 | | 8/2005 | Alphonse |
| 7,068,905 B2 | * | 6/2006 | Vakhshoori et al. ......... 385/129 |
| 7,103,081 B2 | * | 9/2006 | Nomaguchi ............... 372/49.01 |
| 7,391,520 B2 | | 6/2008 | Zhou et al. |
| 7,557,931 B2 | | 7/2009 | Toida |
| 7,697,145 B2 | | 4/2010 | Izatt |
| 7,826,059 B2 | | 11/2010 | Roth et al. |
| 7,848,791 B2 | | 12/2010 | Schmitt et al. |
| 7,872,761 B2 | | 1/2011 | Pedro et al. |
| 2009/0213882 A1 | * | 8/2009 | Weida et al. ................ 372/23 |
| 2009/0262359 A1 | | 10/2009 | Bajraszewski et al. |

OTHER PUBLICATIONS

De Boer, J.F., et al., "Improved signal-to-noise ratio in spectral-domain compared with time-domain optical coherence tomography", Optics Letters, 2003, pp. 2067-2069, 28-21, p. 2067-2, Optical Society of America, USA.

Leitgab, R.C., Hitzenberger, C.K. and Fercher, A.F., "Performance of Fourier domain vs. time domain optical coherence tomography", pp. 889-894, Optics Express, 2003. 11 (8 ), Optical Society of America.

Alphonse, G.A. Gilbert, D.B., Harvey, M.G. and Ettenberg, M., "High-Power Superluminescent Diodes", IEEE Journal of Quantum Electronics, pp. 2454-2457, 24, 1988, IEEE, USA.

(Continued)

*Primary Examiner* — Michael A Lyons
(74) *Attorney, Agent, or Firm* — Sonali Banerjee

(57) ABSTRACT

A new broadband discrete spectrum light source comprising a gain medium placed in a feedback cavity is disclosed. A design for a feedback cavity including reflectors having raised-edge reflectivity is presented. Bandwidth enhancement is achieved by selectively enhancing the intensity of the discrete emission lines near the band edges of the gain medium spectrum. The bandwidth of a broadband discrete spectrum light source is further enhanced by digitally applying a spectral correction to each detected signal according to a predetermined correction profile. A combined effect of using a broadband discrete spectrum light source and applying spectral correction to the detected signal in an imaging system such as a Spectral Domain Optical Coherence Tomography (SD-OCT) imaging system, results in a desired spectral profile and a bandwidth necessary to achieve higher depth resolution for obtaining high quality diagnostic images.

24 Claims, 11 Drawing Sheets

OTHER PUBLICATIONS

Henry, C.H., "Theory of Spontaneous Emission Noise in Open Resonators and its Application to Lasers and Optical Amplifiers", IEEE Journal of Lightwave Technology, pp. 288-297, LT-4, 1986, IEEE, USA.

Alphonse, G.A., "Design of High-Power Superluminescent Diodes with Low Spectral Modulation", Proceedings of SPIE, pp. 125-138, vol. 4648, 2000, SPIE USA.

Vasallo, C., "Polarization-independent antireflection coataings for semiconductor optical amplifiers", Electronic Letters, pp. 61-62, vol. 24, 1988, IEEE, USA.

Alphonse, G.A. and Toda, M., "Mode Coupling in Angled Facet Semiconductor Optical Amplifiers and Superluminescent Diodes", IEEE Journal of Lightwave Technology, pp. 215-219, 10, 1992, IEEE, USA.

* cited by examiner

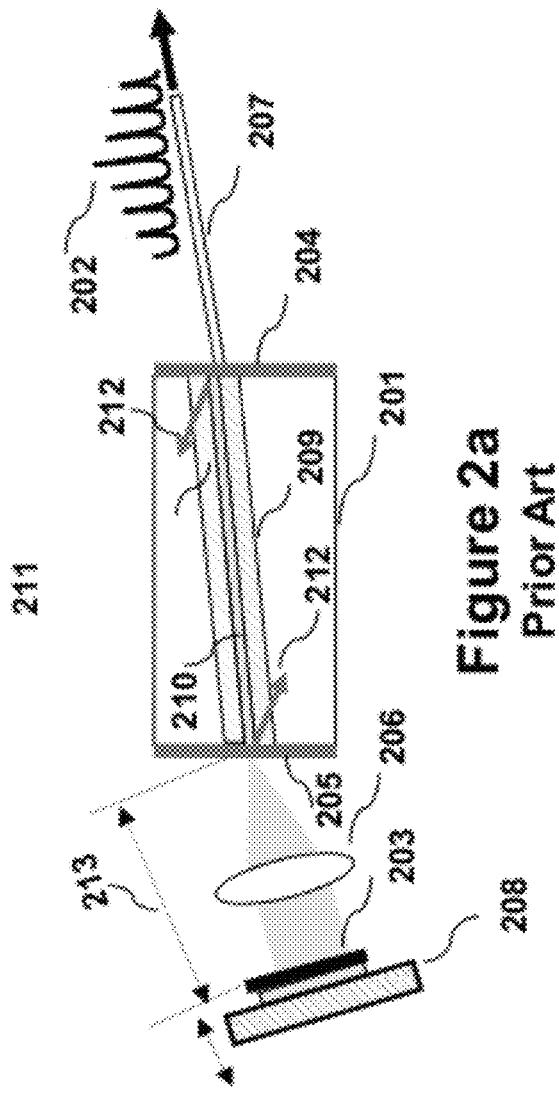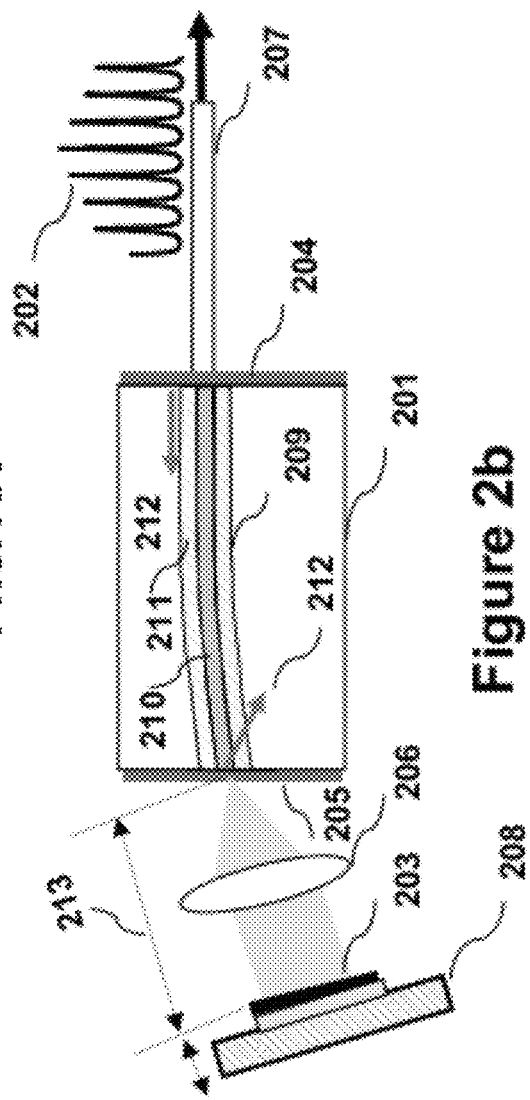
Figure 2a
Prior Art
Figure 2b
Prior Art

BROADBAND DISCRETE SPECTRUM OPTICAL SOURCE

CROSS REFERENCE TO RELATED APPLICATION

This application is a Continuation-In-Part (CIP) application of the U.S. patent application Ser. No. 13/111,047 filed on May 19, 2011, by the inventor of this application, and claims priority from said co-pending application which in turn claims priority from U.S. Provisional Patent Application No. 61/396,284 filed on May 26, 2010. The contents of above identified applications, is hereby 'incorporated by reference' in their entirety.

BACKGROUND OF THE INVENTION

1. Field of the Invention

This invention relates to the field of Optical Coherence Tomography (OCT) imaging system and in particular, to a broadband discrete spectrum optical source and a method for enhancing the bandwidth of an OCT imaging system.

2. Description of the Related Arts

Optical Coherence Tomography (OCT) is a fast and accurate optical imaging technique, frequently used in producing high-resolution images for a variety of diagnostics and clinical applications. Currently, most common commercial application of OCT is primarily in the field of ophthalmology which provides eye clinicians the ability to quantify retinal nerve fiber layers by direct thickness measurements of the retina. As an imaging method, it offers diagnosis and care of eye diseases such as a glaucoma, macular degeneration, diabetic retinopathy (damage to retinal blood vessels) to name just a few. As the technology matures and becomes cost effective, applications of OCT may be expanded to other emerging applications in fields that includes but are not limited to, cardiology, dentistry, cancer diagnosis, glucose monitoring, and dermatology in near future.

Primarily, OCT is an interferometric technique in which the light from a broadband or a tunable source is split into a reference arm and a sensing arm of an interferometer. Light from the two arms are recombined and allowed to interfere at a detection system. The detected interferometric signal is processed in time domain or frequency domain, to obtain an image of a sample-for example, a retina or a fundus in ophthalmological diagnostics. An important condition to detect an interference signal is that the optical path difference between the two arms of the interferometer is shorter than the coherence length of the light source.

OCT can be configured to operate in a "time domain" (TD-OCT) imaging mode or in a Fourier-domain (FD-OCT) imaging mode. While TD-OCT system is accurate, some of the limitations are complexity, relatively low speed of mechanical scanning devices, and low source output power resulting in low imaging speed. These and other limitations are well documented in the co-pending U.S. patent application Ser. No. 13/111,047 and references cited therein, all of which in their entirety is being incorporated by reference here.

An FD-OCT system offers about 100 times more sensitivity and about 50-100 times faster image acquisition speed. Two equivalent FD-OCT configurations are currently being considered particularly for medical applications—a Swept Source (SS)—OCT configuration and a Spectral Domain (SD)-OCT configuration. With the same average source power, the performances of the SS-OCT system and SD-OCT system are identical regarding data acquisition and return loss. However, there are differences in system cost, complexity, speed, and depth resolution capability. Several advantages of an SD-OCT system over SS-OCT system described in other United States Patents, is summarized in the co-pending U.S. application Ser. No. 13/111,047. That disclosure is being incorporated by reference in its entirety.

A common drawback of the SD-OCT system described in the reference patents is that the broadband light sources such as, a Super Luminescent Diode (SLD) or an Amplified Spontaneous Emission (ASE) light source used in these prior art OCT systems exhibit low power density. Therefore power received at each detector of a detector array is relatively low, resulting in low image sensitivity. In order to improve image sensitivity, a longer signal integration time is required at the detector array thereby, limiting the speed of imaging. Imaging speed for the SD-OCT can be improved by increasing the signal level received at the detectors so as to reduce integration time at the detector.

The interference signal in a SD-OCT system is generated using light from a broadband source. Therefore a dispersive device such as a grating is necessary to separate the combined reference and sensing lights into its spectral components. Each spectral component can then be individually detected using a photo-detector array and addressed sequentially, to produce a digital spectrum (or a trace) of the interference signal. The detector signals from the detector array can be read out at a much faster rate than the source scanning rate in a SS-OCT system because source scanning is a mechanical process having its own limitations.

Despite its limitations, SD-OCT system is widely used in ophthalmology due to its simplicity and capability to produce quality 3D retinal images free from artifacts resulting from natural eye motion, at a reasonable cost. To produce spectrally smooth good quality image, the output power level of the order of a few mW (milliwatts) from a SLD's used currently in a SD-OCT system is insufficient. While data acquisition time for a single line scan (a so-called B-scan) is acceptable (less than a second), the time required to acquire hundreds of line scans to generate a quality 3D image is too long for patient's comfort.

In order to obtain better image quality and speed, higher optical power per detector element is necessary, while remaining within safe limits to prevent tissue damage (for example, retinal tissue). Higher power (10 to 100 times more photons per detector element) translates into shorter exposure time, deeper tissue penetration, and higher readout speed, frame rate, and sensitivity. The shorter exposure time would also enable the use of frame averaging to improve image quality in addition to reducing the total acquisition time of high-resolution 3-D images (also called "C-scans"). The preferred total exposure time for avoiding artifacts caused by natural eye motion and fixation drift is of the order of 3 seconds.

In the co-pending U.S. patent application Ser. No. 13/111, 047, an OCT imaging system using a discrete spectrum high power optical source (also referred as light source or source, hereinafter) is disclosed. As disclosed therein, a high output power light source in the imaging system is configured using a gain medium such as semiconductor optical amplifier (SOA) or a SLD, placed within a reflective feedback optical cavity comprising two reflectors. High power output from the light source is achieved by designing the optical cavity such that the reflectivity of the front reflector is very low, of the order of $10^{-5}$ to $10^{-6}$; the reflectivity of the back reflector and gain are adjusted to obtain a desired output power. The output spectrum of such a light source exhibits a set of discrete emission peaks resembling teeth of a comb (a "COMB"

source). In one variation of the discrete spectrum source, the back reflector is placed external to the gain medium at an adjustable distance from the gain medium.

In a preferred embodiment disclosed in the co-pending U.S. patent application Ser. No. 13/111,047, low facet reflectivity is achieved by tilting (preferably by about 6 degrees) the gain medium of a SOA waveguide with respect to the facet normal. In another preferred embodiment, the gain medium waveguide is perpendicular to the front facet and tilted with respect to the back facet of the gain medium device such that the waveguide is a bent or curved waveguide. The tilted or bent gain media reduces the natural back reflection from the waveguide facet and enables the extension of the cavity to a back reflector placed at some adjustable distance from the gain medium.

This invention provides a new broadband discrete spectrum light source comprising a gain medium placed within a feedback cavity that is designed to significantly extend the bandwidth of over a prior art discrete spectrum light source. When used in an OCT imaging system, the overall spectral profile and bandwidth of the discrete spectrum light source may be further enhanced by at least a factor of two, by applying signal processing methods to the detected interference signal. When used in a SD-OCT imaging system, the broadband discrete spectrum light source together with the signal processing method disclosed in this invention would improve depth resolution, sensitivity and speed of imaging over currently available SD-OCT imaging systems.

SUMMARY OF THE INVENTION

A new broadband light source is provided for a high sensitivity and high speed SD-OCT imaging system. The new broadband light source is configured with a gain medium disposed between two reflectors in a feedback cavity, such that light from the gain medium undergoes multiple reflections between the reflectors. Consequently, the in-phase components of light is amplified within the feedback cavity giving rise to a spectral profile characterized by a discrete set of sharp emission lines (discrete spectrum) having high output power in each emission line well beyond the band edges of the gain medium spectrum. The new broadband source exhibits a bandwidth that is at least 50% more than the bandwidth of a prior art discrete spectrum light source of similar dimension.

In an embodiment of the broadband light source the feedback cavity is configured using a very low reflectivity front reflector and a high reflectivity back reflector, such that the cavity gain is adjusted to operate in a linear amplifier mode without ever reaching a lasing threshold at any wavelength. The overall output spectrum of the gain medium without any feedback from the cavity resembles the optical spectrum of a SLD, whereas when the cavity provides feedback to the gain medium by multiple reflections within the cavity, the spectral profile of the broadband light source exhibits a discrete set of individual emission lines having high output peak power resembling teeth of a comb ('COMB' source).

In one embodiment a broadband light source is configured using an optical gain medium placed within a feedback cavity constructed of a back and a front reflector such that the reflectivity as a function of wavelength, of the back and/or front reflectors exhibit raised-edge reflectivity profile. The raised-edge reflectivity profiles exhibit higher reflectivity at the band edges where the gain of the gain medium spectrum falls off to a prescribed level. Since the product of gain of the gain medium and the reflectivity determines the output power, the intensity of the discrete spectral emission peaks towards the band edges is enhanced. Consequently, the bandwidth of the discrete spectrum light source is extended beyond the band edges of the gain medium spectrum.

In a different embodiment a broadband light source is configured by placing a gain medium in a feedback cavity where the back and/or front reflectors of the feedback cavity is constructed as an etalon. Refractive index and thickness of the etalon material is selected as design parameters to obtain a desired reflectivity value as well as a reflectivity profile as a function of wavelength. The front and back reflectors are designed independently to achieve different reflectivity values, for example, the front reflector is selected to have a lower reflectivity than the back reflector. The etalon may comprise a single layer or a stack of layers including quarter wavelength layers (hereinafter quarterwave layers), half wavelength layers (hereinafter halfwave layers), a combination thereof, at a center wavelength of the gain medium, or a double pass Bragg grating, deposited on a reflective substrate. An etalon so constructed exhibits raised-edge reflectivity profile, and is suitable to enhance the bandwidth of the broadband discrete spectrum light source.

In another embodiment of a broadband discrete spectrum light source at least one reflector of the feedback cavity is external to the gain medium. In one preferred embodiment of an external feedback cavity, the back reflector is external to the cavity and the front reflector is constructed on one facet of the gain medium. In one variation of the broadband discrete spectrum light source using an external back reflector, spatial distribution of each emission line in the spectral profile is made to match the spatial distribution of detectors in a detector array for efficient detection of all the spectral components simultaneously.

In an alternative embodiment, a feedback cavity may be constructed directly on the end facets of a gain medium. In one variation of such a broadband discrete spectrum source, the back and the front reflectors of the feedback cavity are disposed on the end facets of the gain medium such that the end facets of the gain medium forms the feedback cavity.

In one embodiment, the gain medium is a semiconductor optical amplifier (SOA) or a SLD structure constructed from semiconductor waveguide. In some variant embodiments the waveguide structure is a straight waveguide, a tilted waveguide, a bent or a curved waveguide SOA structure. In another variation, a gain medium comprising a semiconductor laser chip having a straight waveguide structure with perpendicular end facets is placed in a feedback cavity designed according to this invention so as to provide a controlled amplification, such that the cavity gain is adjusted to operate in a linear amplifier mode without ever reaching a lasing threshold at any wavelength supported by the feedback cavity. The resulting structure functions as a broadband discrete spectrum source without lasing.

In another embodiment of a broadband light source additional enhancement of bandwidth is achieved by applying an arithmetic operation to a digital spectrum of a detected interference signal before applying a Fourier Transformation (FT) for imaging. A preferred arithmetic operation includes multiplying each element of the detected signal by a corresponding digitally generated correction function in an electronic processor using software tools, such that the weaker signals detected at the band edges of the gain medium spectrum are electronically boosted. In one variation of applying the arithmetic operation, the correction function is generated from the detected signal and signal to noise ratio consideration.

In a preferred embodiment of a broadband light source bandwidth enhancement of about a factor of 2 over the gain medium spectrum is achieved by placing the gain medium in a feedback cavity constructed using reflectors having raised-edge reflectivity and applying arithmetic operation to the detected interference signal in tandem.

In one embodiment of the invention a SLD in a SD-OCT system is replaced by a new broadband light source having extended bandwidth such that the spatial distribution of the discrete spectral line matches spatial distribution of detectors in a detector array so as to significantly improve OSNR (Optical Signal to Noise Ratio), depth resolution and imaging speed.

In another embodiment of the invention, a SD-OCT system includes a broadband discrete spectrum light source where each emission line of the light source is matched with a detector in the detector array. Interference signals detected in each detector of the detector array is digitally enhanced by applying a predetermined correction to the weaker detected signal in a signal processor such that the detection of interference signal is extended beyond the band edges of the source spectrum.

In another embodiment of the invention, a SD-OCT system applies a predetermined correction to the weaker detected signal according to a digitally generated correction signal obtained from the interference signal detected in the detector array. In operation, the digitally generated correction signal may be stored in the processor or generated using software operations on the detected interference signal.

In another embodiment of the invention, a SD-OCT system includes a broadband discrete spectrum light source including a prior art source, and a post-detection arithmetic operation is performed using signal processing to increase the magnitude of the weak components of the detected signals at the edges and/or other parts of the spectrum to increase the effective bandwidth for improving the image quality.

BRIEF DESCRIPTION OF THE DRAWINGS

Various aspects of the invention disclosed in the detailed description section of this application will be better understood in view of the drawing figures in which:

FIG. 2a and FIG. 2b show two different preferred embodiments of prior art discrete spectrum light sources;

DETAILED DESCRIPTION OF THE INVENTION

Different combinations and sub-combinations of different aspects are shown and described in different preferred embodiments. For clarity and ease of discussion, each drawing figure shows a particular aspect or a combination of few aspects that may be implemented in an embodiment either alone or, in combination with one or more different aspects shown in other embodiments of the invention within the framework of the principles of the invention to be described later. An element not shown in any particular embodiment is not to be construed as precluded from the embodiment unless stated otherwise.

Figure 1:
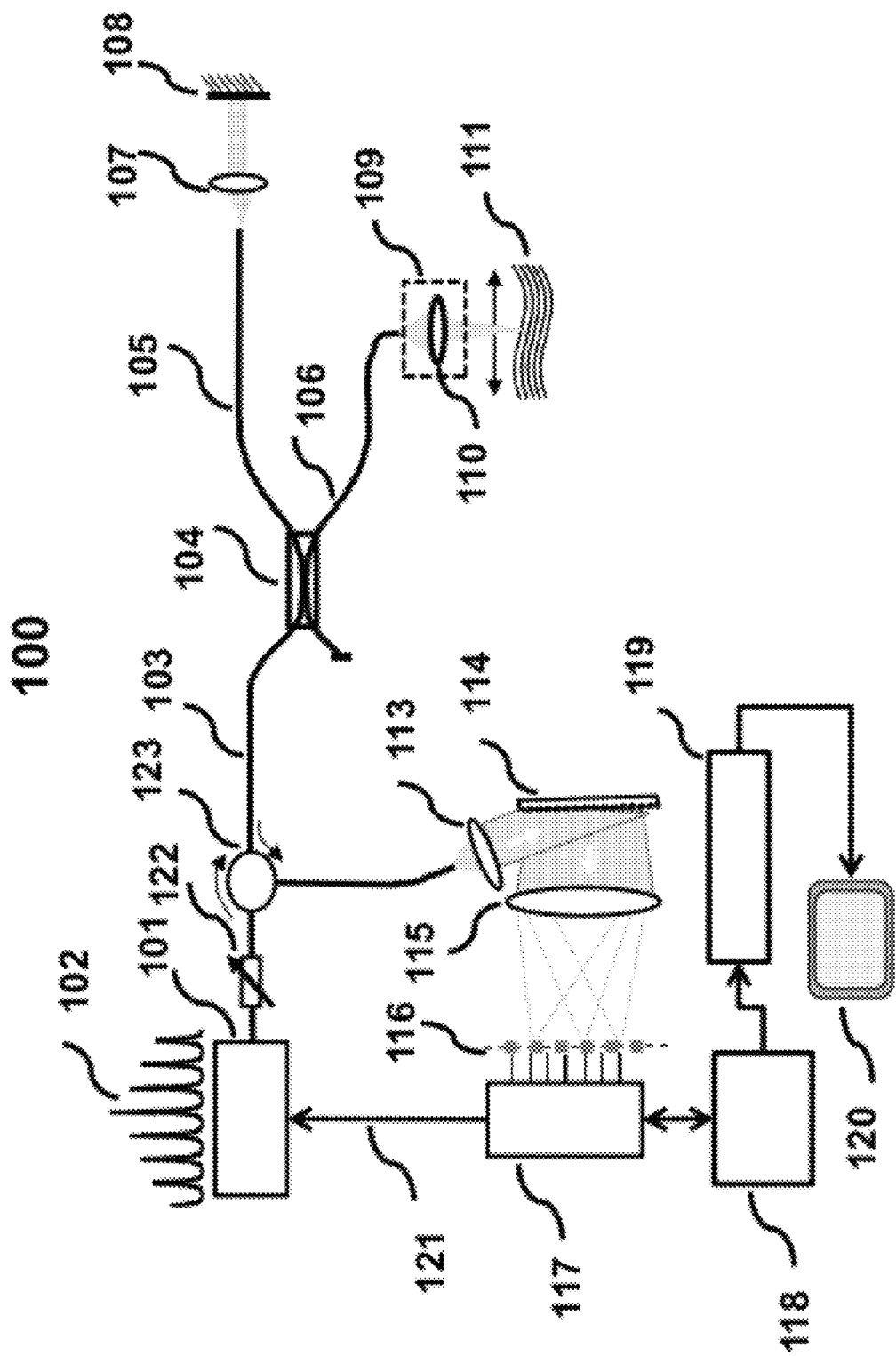
FIG. 1 is a schematic representation of a prior art spectral domain (SD) optical coherence tomography (OCT) system.

FIG. 1 shows a prior art OCT imaging system 100 disclosed in the co-pending U.S. patent application Ser. No. 13/111,047 filed on May 19, 2011, content of which is being incorporated by reference in its entirety. The prior art system disclosed therein is configured using a discrete spectrum light source 101 that exhibit a 'COMB' type optical spectrum 102. A splitter/combiner 104 divides the input light 103 into a reference arm 105 and a sensing arm 106, respectively, of an interferometer. Since it is important that light going to the sensing arm 106 is within a permissible safe limit to prevent tissue damage, output from the light source is coupled to the interferometer via an optional variable attenuator 122 preferably with a power level monitor (not shown here), and a circulator 123 to isolate the input light from the combined light that generates an interference signal after being detected in the detector elements.

In the sensing arm, focusing optics 110 of a two-dimensional scanner 109 focuses the light onto a sample 111. The light traversing the round trip path from the reference and the sensing arms are recombined in the splitter/combiner and the combined signal 112 is collimated by a collimating optics 113 and directed to a dispersion device 114. The dispersion device generates different wavelength components that are focused by a focusing optics 115 onto elements of a detector array 116 which creates the wavelength components of the interference signal. A selector switch 117 directs the interference signal detected by the detector array through a Fast Fourier Transform (FFT) device 118 (or through a software operation) and a signal processor 119 generates a trace which is a depth profile of the selected location in the sample. The aggregate of the collected traces constitutes an image of the sample. The sample image is displayed on a display device 120. The selector switch also provides a trigger signal 121 to control the imaging cycle.

FIGS. 2a and 2b schematically show two different embodiments of prior art discrete spectrum light sources that may be used in the OCT system shown in FIG. 1. The parts that are equivalent or provide similar functions are labeled identically in FIGS. 2a and 2b. The light sources shown in FIGS. 2a and 2b are configured using a reflective cavity comprising a movable high reflectivity back reflector 203 that is external to the gain medium 209 and a low reflectivity front reflector 204 that is coated on a facet of the gain medium. The gain media in the exemplary embodiments comprise a tilted or a bent semiconductor waveguide structure, respectively, as shown in FIGS. 2a and 2b. The output optical spectrum from these types of sources exhibit discrete emission lines—the spectral range (FSR)—or the 'pitch' (spatial distribution) of the emission lines is adjusted by moving the back reflector mounted on a translation equipment 208 and the output power is adjusted by adjusting the gain of the gain medium.

Figure 3:
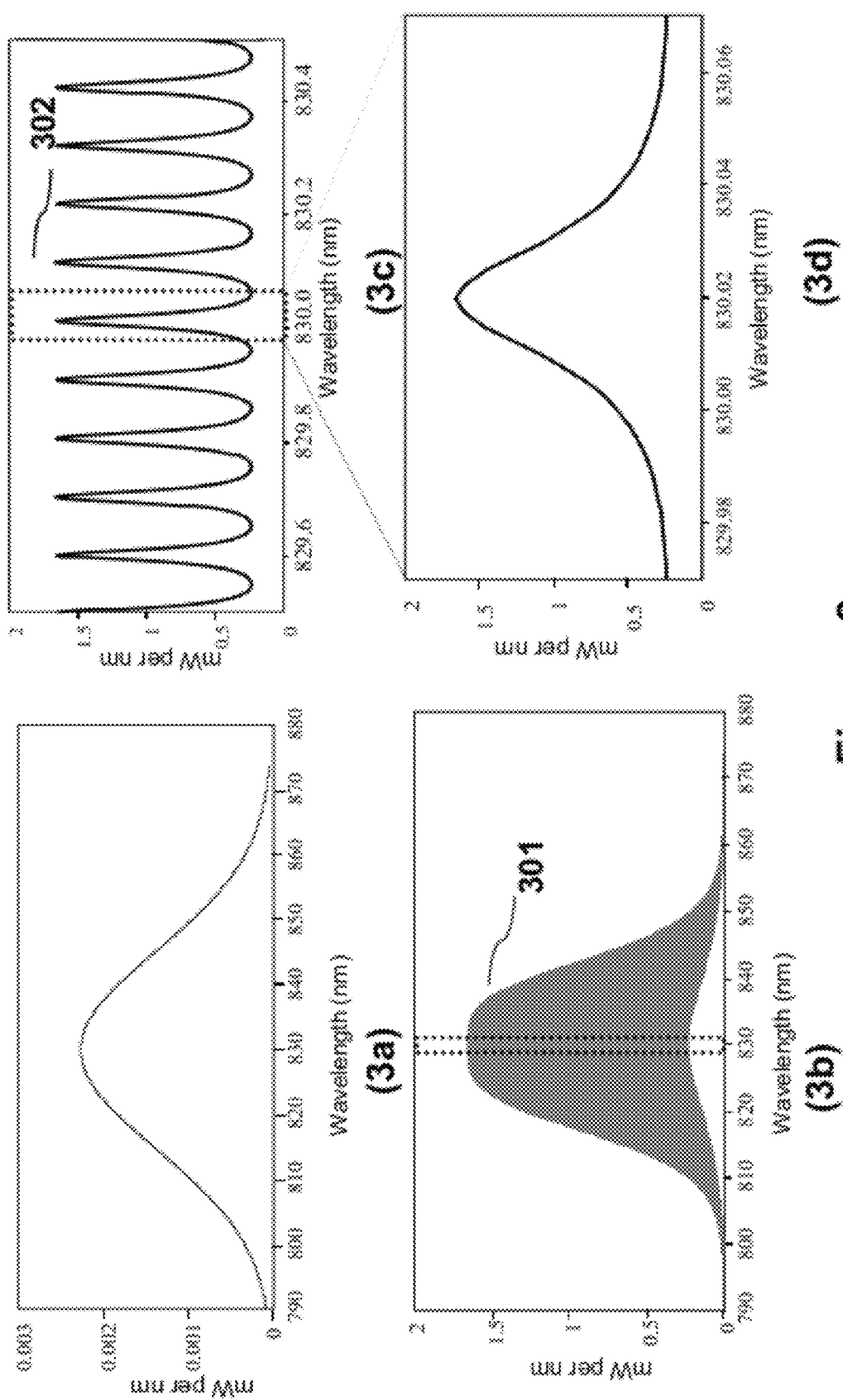
FIG. 3 represents typical spectral profile of a SLD compared with spectral profile of a prior art discrete spectrum light source:
(a) spectral profile of a SLD,
(b) spectral profile of a prior art discrete spectrum light source,
(c) expanded spectral profile of a prior art discrete spectrum light source at the center of the spectrum, and
(d) spectral profile of a prior art discrete spectrum light source at high resolution showing a near Gaussian line shape at the center of the spectrum.

Simulation results for an exemplary spectral density calculation are shown in FIG. 3 for a SLD and a discrete spectrum source having similar physical parameters for example, length L=1 mm, effective refractive index $n_e$=3.34, and spectral bandwidth $\Delta\lambda$=50 nm. In all the spectra shown in FIG. 3 the x-axis represent wavelength (in nm) and the y-axis represents optical power (in mW/nm). More specifically, calculated optical spectrum of the new broadband source and several expanded views of the center of the spectrum are shown in FIGS. 3b, 3c and 3d, respectively.

Referring now to FIG. 3, an optical spectrum of a SLD is shown in the graph 3a for a comparison with optical spectra from a discrete spectrum source shown in graphs 3b, 3c and 3d. It should be noted that the y-axis scale in graph 3a is different than the other graphs namely 3b, 3c and 3d, respectively. It is important to note that the peak power in each emission line in graphs 3b, 3c and 3d, is significantly higher than the output power of the broad SLD spectrum shown in graph 3a. In the full spectrum plot of the discrete spectrum light source shown in graph 3b, the individual lines are not discernible because of their sheer number and close spacing.

The central portion of the spectrum 301 shown enlarged in graph 3c, exhibits comb-like "teeth" comprising a group of narrow individual emission lines at the cavity resonance peaks with a spacing 82 between them. A further expansion of the spectrum around a single line 302, shown in graph 3d depicts an individual emission line that resembles a narrow laser line spectrum (Gaussian-like) having a Full Width at Half Maximum (FWHM) Ω. The spacing δλ is usually referred to as the Free Spectral Range (FSR), and the width Ω is referred to as the linewidth of laser-like spectral lines.

The line spacing or Free Spectral Range (FSR) near the central wavelength $\lambda_c$ for a discrete spectrum light source is written as—

$$FSR = \delta\lambda = \frac{\lambda_c^2}{2(n_e L + d)} \tag{1}$$

The line spacing for the discrete source is very narrow. For example, for a gain medium comprising a SOA waveguide having a refractive index of 3.34, and length 1.0 mm operating at a center wavelength of 830 nm, with the back reflector placed on the SOA back facet (d=0), the FSR is of the order of one Angstrom. Placing the back facet at an adjustable distance from the SOA allows varying the line spacing such as to match the pattern of the SD-OCT's detector elements in a detector array.

The resolution of an OCT system, or the ability to discern adjacent features in an image, is given by the coherence length $L_c$ ($L_c$=0.44$\lambda_c^2$/Δλ) of the light source, where Δλ is the half-power bandwidth B. Thus, the resolution is inversely proportional to the light source bandwidth. The light source in typical ophthalmic SD-OCT systems has $\lambda_c$ of about 800 to 860 nm (nanometers) and λΔ of about 26 nm, which gives a resolution of about 12 microns. The retinal thickness is about 100 microns and contains several layers, some of which are only a few microns thick. While the resolution of standard OCT can accurately measure the overall retinal thickness, a higher resolution is needed in order to discern smaller features.

For better accuracy and in particular, for accuracy in medical imaging applications, a resolution of 5 microns or better is preferred, which is not possible to achieve using a single SLD source. An alternative way to increase the source bandwidth is to stagger two or more SLDs with overlapping spectra onto a single fiber. While a combination source improves the bandwidth to some extent, it does not increase the power per detector element. In addition, a combination source is more expensive because of the time and effort needed to select and match SLDs with the appropriate overlapping spectra.

As disclosed in the co-pending U.S. patent application Ser. No. 13/111,047 discrete spectrum light source provide significant improvement over SLD source in OCT systems.

However, the prior art discrete spectrum source does not necessarily provide significantly improved bandwidth or image resolution. The broadband discrete spectrum source disclosed in this invention provides significant improvement in output power, bandwidth and consequently, better image resolution. The bandwidth of a discrete spectrum light source may be enhanced to provide OCT resolution of about 5 to 6-micron. Staggering two such sources onto a single fiber can achieve resolution of about 2 to 3 microns. One way to achieve higher bandwidth from a single discrete spectrum light source is to configure the feedback cavity with front and back reflectors having raised-edge reflectivity such that the feedback factor (the product of the gain medium gain and the square root of the product of front and back reflectivity) is enhanced at the band edges to overcome the naturally occurring gain fall-off at the band edges of the gain medium.

It will be described shortly that the bandwidth of a discrete spectrum source disclosed in the U.S. patent application Ser. No. 13/111,047 may be broadened by two different methods. The methods may be implemented separately or in a suitable combination. In the first method, a gain medium comprising a discrete spectrum light source is placed in an external reflective cavity having a predetermined spectral profile. More specifically, a feedback cavity exhibiting raised-edge reflectivity is designed to offset falling gain at the band edges of the gain medium.

In the second method, the interference signal detected at the detector array is digitally enhanced near the band edges using signal processing tools. By applying a correction using signal processing tools, the detected signal at each detector of the detector array is digitally modified. In particular, detected signal at the band edges of the gain medium spectrum is enhanced by a predetermined amount previously stored in the processor so as to enhance the overall bandwidth of the detection system. One advantage of the digital enhancement at the systems level is that besides improving the bandwidth further, it can also be used to modify the spectral profile of the detected signals in any desired manner. For example, it is known that a Gaussian profile is an ideal spectral profile to avoid generation of sidebands. The method described here can easily be used to convert the profile of the detected spectrum into a broadband Gaussian and thus improve image quality as well as resolution by reducing or removing sidebands.

In the following discussion although each method will be described separately for ease and clarity, combining the two methods is not precluded. Furthermore, different aspects of each method will be described using different embodiments. Each embodiment described in the following sections merely shows one or more aspect and may be used in different combinations and sub-combinations thereof for practicing the invention in different modes. Other combinations and sub-combinations that may occur to a person of ordinary skill in the art are not precluded.

Bandwidth Enhancement—a New Feedback Cavity Design:

Referring now to FIGS. 2a and 2b, there it shows prior art discrete spectrum light sources disclosed in the co-pending U.S. patent application Ser. No. 13/111,047. The prior art sources comprise a semiconductor gain medium 201 disposed within an external reflective cavity formed by the front reflector 204 and a back reflector 203, respectively. The discussion is equally pertinent to other gain media that includes but is not limited to, SLD, SOA, an ASE source, a solid state gain medium, an optical fiber, etc.

As disclosed in the co-pending U.S. patent application Ser. No. 13/111,047, the output power of a discrete spectrum light source (COMB) having a back reflector placed directly on the back facet of the gain medium waveguide may be written (distance between the back reflective surface and the back facet of the gain medium d=0), as $$P_{COMB} = P_{SLD}\left[\frac{(1-R_2)(1+R_1 G_s)}{1+K^2-2K\cos\left(\frac{4\pi n_e L}{\lambda}\right)}\right] \quad (2)$$

where, $$P_{SLD} = P_{sp}(G_s - 1), \; K = G_s\sqrt{R_1 R_2}, \; G_s = \exp(g_0 I - \alpha L)$$

In Eq. 2, $P_{sp}$ is the spontaneous emission power (of the order of 0.0015 to 0.003 mW for a typical semiconductor gain medium), $P_{SLD}$ is the output power of the gain medium without feedback reflections, $G_s$ is the gain of the gain medium, $R_1$ and $R_2$ are the back and front reflectance, respectively, of the reflective cavity, $g_o$ is the semiconductor peak gain coefficient (about 0.054/mA), I is the drive current, $\alpha$ is the absorption coefficient of the semiconductor gain medium, and L the semiconductor chip length. Not mentioned in that equation was the fact that $G_s$ has a Gaussian-like spectrum with a specific half-power bandwidth around a center wavelength $\lambda_c$.

In order to understand the necessary conditions leading to bandwidth enhancement according to this invention, it is useful to review the spectral dependence of the gain medium (gain medium spectrum). The Gaussian-like dependence of the semiconductor gain medium stems from the fact that the gain coefficient is not just the constant $g_o$, but is the function of wavelength of the form—

$$g_o(\lambda) = g_o \exp\left[-p_o^2 (\lambda - \lambda_c)^2\right], \quad (3)$$

where $$p_o = \frac{2\sqrt{\ln 2}}{B_o}$$

In Eq. 3, $\lambda$ is any arbitrary wavelength within the range of operation of the gain medium and $B_o$ is the spontaneous emission bandwidth, which is of the order of 90 to 100 nm for a typical semiconductor gain medium. $B_o$ is the bandwidth that would be exhibited by the gain medium if operating as an LED or as a source of spontaneous emission at low gain. Accordingly, the gain $G_s$ will henceforth be written in its wavelength dependent form as $G_s(\lambda)$, which, when expanded in approximate power series of $g_o(\lambda)$, can be written as—

$$G(\lambda) = G_o \exp\left[-p^2 (\lambda - \lambda_c)^2\right], \quad (4)$$

where, $$G_o = \exp(g_o I - \alpha L), \; p = \frac{2\sqrt{\ln 2}}{B}, \; B \approx \frac{B_o}{\sqrt{\ln G_o + \alpha L}}$$

It may be recalled that $G_s$ in Eq. 2 is now the peak gain $G_o$ and that B is the bandwidth of the gain medium at a drive current I. From Eq. 4, it can be appreciated that due to the factor in the denominator of the bandwidth expression for B, the bandwidth B is narrower than the spontaneous emission bandwidth $B_o$. This point is advantageously exploited for the design of the broadband discrete spectrum source. A commercial SLD requires $G_o$ of the order of 6000 to 10,000 to produce 20 to 30 mW of output power, whereas a discrete spectrum light source according to this invention needs a $G_o$ of less than 200 to yield a higher output power. The bandwidth of a standard commercial SLD is of the order of 25 nm, whereas for a gain medium of a discrete spectrum light source a gain value of 200 would result in a bandwidth of about 36 nm. Therefore, gain and reflectivity of a discrete spectrum light source may be selected appropriately to achieve a desired output power and bandwidth.

Due to the wavelength dependence of the gain, the output light also has a wavelength-dependent power density. Thus, $P_{SLD}$ the power when both $R_1$ and $R_2$ are zero, i.e., in the absence of feedback, not to be confused with the power of a standard commercial SLD) is replaced by $P_{SLD}(\lambda)$ and the feedback factor K is replaced by $K(\lambda)$ in Eq. 2, such that $$P_{SLD}(\lambda) = P_{SP}[G_s(\lambda)-1],$$

and $$K(\lambda) = G_s(\lambda)\sqrt{R_1 R_2} \quad (5)$$

For the purpose of explaining the bandwidth enhancement, focus will be placed on the overall spectral profile of the discrete peaks, i.e., $P_{COMB}(\lambda)$ at the values of $\lambda$ for which the cosine term in Eq.2 becomes unity. Then for $R_2 \ll R_1$ and $G_s(\lambda) \gg 1$, necessarily required for implementing the discrete spectrum light source, the output power profile can be written from Eq. (2) as $$P_{COMB}(\lambda) \approx P_{SLD} \frac{R_1 G_s(\lambda)}{[1-K(\lambda)]^2} = P_{SP}\left\{\frac{R_1 G_s^2(\lambda)}{\left[1-G_s(\lambda)\sqrt{R_1 R_2}\right]^2}\right\} \quad (6)$$

The quantity in the large brackets is the gain spectrum with feedback, which differentiates the discrete spectrum light source from an SLD. The gain profile is high because it is proportional to the back reflector reflectivity and the square of the gain, and inversely proportional to the denominator $[1-G_s(\lambda)(R_1R_2)^{1/2}]^2$. The latter can significantly contribute towards increasing the net gain when the value of $G_s(\lambda)(R_1R_2)^{1/2}$ is allowed to approach unity. The output power $P_{SLD}$ of an SLD made from the same gain medium is $\sim P_{SP} G_s(\lambda)$, i.e., proportional to only $G_s(\lambda)$, and therefore is much lower than the output power of the comb type discrete spectrum light source.

FIG. 3 shows different traces (a)-(d) of power spectral density (in mW/nm) as a function of wavelength for a SLD and a discrete spectrum source using the gain medium operating with a drive current to achieve a gain $G_o$ of 200. The data is presented in terms of the spectral density because it depicts the wavelength dependence more clearly. The total power would be obtained by integration of the spectral density over all wavelengths. In FIG. 3 trace (a) is a spectrum for a SLD and trace (b) is a spectrum of a discrete spectrum source without bandwidth broadening (constant $R_1$ and $R_2$).

It should be noted that the scale shown in the SLD spectral density plot (a) is much lower than the scale for the discrete spectrum source plot (b), indicating that for the SLD, a much lower power density is achieved as compared to the discrete spectrum source. In this example, the total output power for the SLD would be about 0.6 mW, whereas peak power for the discrete spectrum source would be about 436 mW and average power would be about 132 mW. Due to the fact that the discrete output power is proportional to the square of the gain of the gain medium, overall bandwidth is narrower than the bandwidth of the gain medium. Yet, it is comparable to the typical 20-30 mW SLD currently used, albeit with much higher output power.

In the full spectrum plot of a discrete spectrum light source shown in FIG. 3b, the individual lines are not discernible because of their sheer number and close spacing. The central portion of the spectrum 301 shown enlarged in FIG. 3c, exhibits the comb "teeth" as a group of narrow individual emission lines at the cavity resonance peak with a spacing $\delta\lambda$ between them. A further expansion of $\delta\lambda$ around a single line 302, shown in FIG. 3d, depicts an individual tooth as a Gaussian-like and laser-like spectral line of narrower Full Width at Half Maximum (FWHM) $\Omega$. The spacing 82 is usually referred to as the Free Spectral Range (FSR), and the width $\Omega$ is referred to as the linewidth of these laser-like spectral lines. It is important to note that the peak power in each emission line is significantly higher than the output power of the SLD alone (FIG. 3a).

To enhance the bandwidth of the discrete spectrum source a reflective feedback cavity is configured where the reflectivity at the back and the front reflectors $R_1$ and $R_2$ are selected to have wavelength-dependent profiles $R_1(\lambda)$ and $R_2(\lambda)$ such that their values are significantly higher at the band edges of gain medium gain $G_s(\lambda)$ than at mid-band, with an edge to mid-band contrast ratio $R_{(edge)}/(R_{(mid)}$ high enough to offset the gain fall-off at the band edges. In that respect, Eq. 6 for the output power of a discrete spectrum source is rewritten as shown below to explicitly reflect the wavelength dependence of the gain and the reflectivity.

$$P_{COMB}(\lambda) \approx P_{SP}\left\{\frac{R_1(\lambda)G_s^2(\lambda)}{\left[1-G_s(\lambda)\sqrt{R_1(\lambda)R_2(\lambda)}\right]^2}\right\} \quad (7)$$

The designation, back and front reflectors are made only for the purpose of discussion to indicate that the two reflectors are placed such that a light beam traversing between the two reflectors are bounced multiple times between the reflectors. Furthermore, it will be assumed that at least one reflector has a substantially higher reflectivity than the other such that the feedback factor is maintained less than unity, and a fraction of the light from the cavity is tapped as output from the light source at the reflector having the lower reflectivity and therefore will be referred to as the front reflector.

Figure 4:
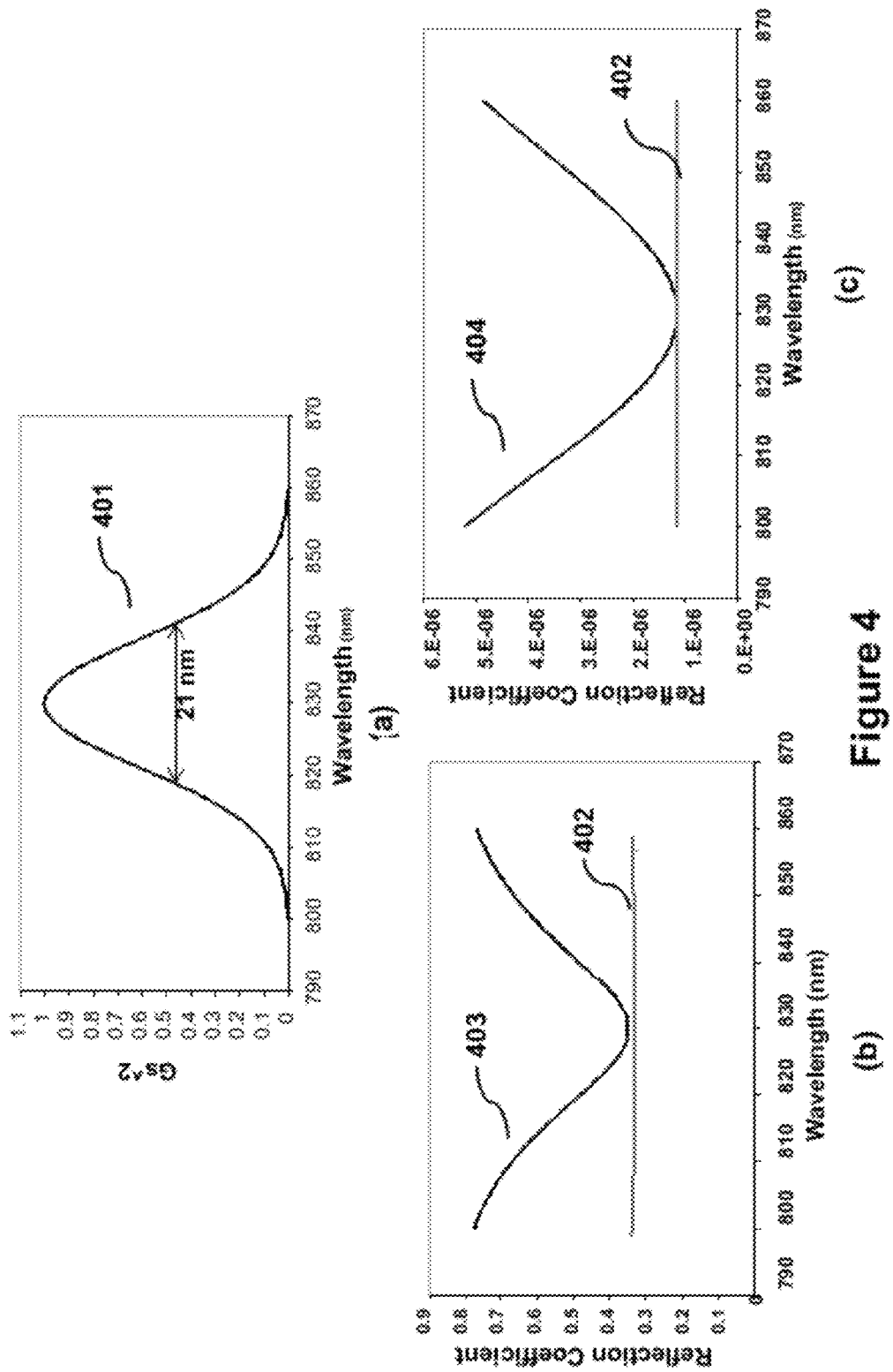
FIG. 4 shows spectral profile of:
(a) square of the gain spectrum of a discrete spectrum light source with flat reflectivity reflector elements;
(b) a raised-edge reflectivity of a back reflector, and
(c) a raised-edge reflectivity of a low reflectivity front reflector.

FIG. 4 shows simulated spectral profile of a gain square $(G_s(\lambda))^2$ of an exemplary gain medium as a function of wavelength in graph (a) and simulated reflection coefficient profile as a function of wavelength for exemplary back and front reflectors in graphs (b) and (c), respectively. In graph (a) depicting the spectrum profile 401 of gain square $(G_s(\lambda))^2$ the band edges drop off quite rapidly with a half-power bandwidth of only ~21 nm. FIG. 4(b) shows exemplary simulated reflection coefficient $R_1(\lambda)$ of a back reflector plotted on the y-axis as a function of wavelength (x-axis) in which trace 403 shows a raised-edge reflectivity profile as compared to a relatively flat profile shown in trace 402. The flat reflectivity profile 402 is of that of a typical prior art discrete spectrum source with a back reflector design disclosed in the co-pending U.S. patent application Ser. No. 13/111,047 whereas the raised-edge reflectivity 403 is for a back reflector design according to this invention. Calculated reflection coefficient profile $R_2(\lambda)$ as a function of wavelength for an exemplary front reflector design is shown in graph (c) in FIG. 4. A relatively flat reflectivity 402 is for a typical prior art reflector design whereas the raised-edge reflectivity 404 is for an exemplary front reflector designed according to this invention.

It may be recalled that in the prior art discrete spectrum source described in the co-pending U.S. patent application Ser. No. 113/111,047, $R_1$ and $R_2$ were constant and the feedback factor $G_s(\lambda)(R_1R_2)^{1/2}$ showed a maximum at mid-band where $G_s(\lambda)$ is maximum. Accordingly, the value of $[1-G_s(\lambda)(R_1R_2)^{1/2}]^2$ becomes small only at mid-band therefore giving a high value of the quantity in the bracket at mid-band. As $G_s(\lambda)$ falls off at the band edges, the value of the feedback factor approaches zero and the value of $[1-G_s(\lambda)(R_1R_2)^{1/2}]^2$ approaches unity, making the denominator ineffective.

However, if $R_1(\lambda)$ and $R_2(\lambda)$ are wavelength-dependent as shown respectively in traces 403 and 404 in FIGS. 4(*b*) and 4(*c*), their product tend to cancel the effect of the gain fall-off. Returning to Eq. 7, the numerator in the bracket in Eq. (7) is the product of $R_1(\lambda)$ and $G_s(\lambda)^2$. As $G_s(\lambda)^2$ fall off near the band edges, the product in the numerator does not fall off as rapidly for a raised-edge $R_1(\lambda)$. It is also noted that the denominator in Eq. (7) contributes to the overall gain over a broader wavelength range. More specifically, as compared to constant $R_1$ and $R_2$ constant (for example profile 402 in FIG. 4) the product in the denominator $[1-G_s(\lambda)\{R_1(\lambda)R_2(\lambda)\}^{1/2}]^2$ in Eq. 7 remains high for raised edge reflectivity $R_1(\lambda)$ and $R_2(\lambda)$ over a broader wavelength range and therefore the wavelength range for which the denominator remains low is broadened. As a result, raised-edge $R_1(\lambda)$ and $R_2(\lambda)$ is effective in compensating for the gain $G_s(\lambda)$ falling off at the band edges. Therefore, it is possible to achieve high overall gain and thereby high output power, over a broader wavelength range with raised—edge $R_1(\lambda)$ and $R_2(\lambda)$.

Figure 5:
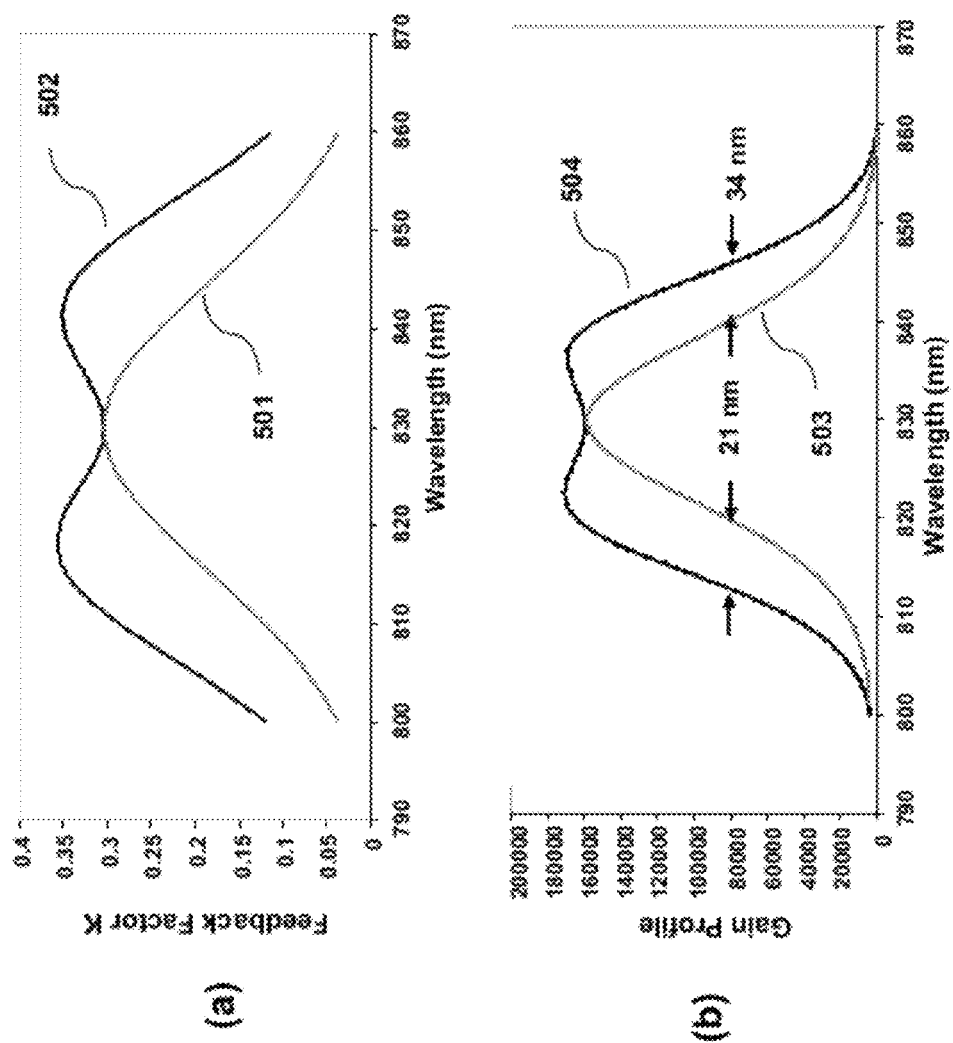
FIG. 5 shows a comparison of:
(a) feedback factor of discrete spectrum light source constructed with flat reflectivity front and back reflectors and with raised-edge reflectivity front and back reflectors, respectively, and
(b) a comparison of gain profile of discrete spectrum source constructed with flat reflectivity reflectors and with raised-edge reflectivity front and back reflectors.

Referring now to FIGS. 4 and 5, simultaneously, a spectral profile of the feedback factor $G_s(\lambda)\{R_1(\lambda)R_2(\lambda)\}^{1/2}$ is shown in FIG. 5(*a*) for an exemplary discrete spectrum light source with back and front reflectors designed to have spectral profiles $R_1(\lambda)$ and $R_2(\lambda)$ shown in FIGS. 4(*b*) and 4(*c*), respectively, together with corresponding profile for a prior art source where $R_1$ and $R_2$ are constant described in the co-pending U.S. patent application Ser. No. 113/111,047. In particular, a trace 502 represents feedback factor for a source designed with raised-edge reflectivity as compared to the feedback factor shown in the trace 501 for a source designed with constant reflectivity. The feedback factor profile 502 with raised-edge reflectivity design extends well beyond the profile 501 with constant reflectivity.

FIG. 5(*b*) shows the overall gain profiles 504 and 503, normalized to unity, for sources designed with the raised-edge reflectivity and with flat reflectivity, respectively. The half-power bandwidth of gain profile 503 with flat reflectivity profile is ~21 nm, whereas it is ~34 nm for the source designed with raised-edge reflectivity shown in trace 504. The increase in bandwidth for this particular design is ~62% (a factor of 1.62). The gain spectrum profile 504 is no longer Gaussian which means that the actual time-domain response will exhibit some low-level sidebands. Computations show that the sidebands are less than 3% of the peak time domain response. The higher the edge-to mid-band reflection contrast, the broader the effective half-power bandwidth up to the point where $G_s(\lambda)$ is too low for effective compensation. Different examples of feedback cavity designs and gain media combinations using single etalons of appropriate thickness, multi-layer etalons, and gratings for achieving reflectivity profiles with high edge-to-mid-band contrast will be described next.

Bandwidth enhancement for a discrete spectrum source is achieved by configuring the back or/and front reflectors of the feedback cavity where at least one reflector, preferably the back reflector, exhibits raised-edge reflectivity profile. In other words, the back and/or front reflector reflectivity exhibit a minimum at mid-band and increase towards the band edges. It is still necessary that the reflectivity of the front reflector be several orders of magnitudes lower than the reflectivity of the back reflector. It is also important to maintain a high contrast ratio between the band-edge and the mid-band to achieve the desired bandwidth enhancement of the overall feedback gain spectrum beyond the natural half-power bandwidth of the gain medium. A different contrast ratio may be selected for the back and front reflector depending upon the desired reflectivity profile for each reflector. A contrast ratio of less than ten may be sufficient in order to achieve a desired bandwidth enhancement.

Figure 6:
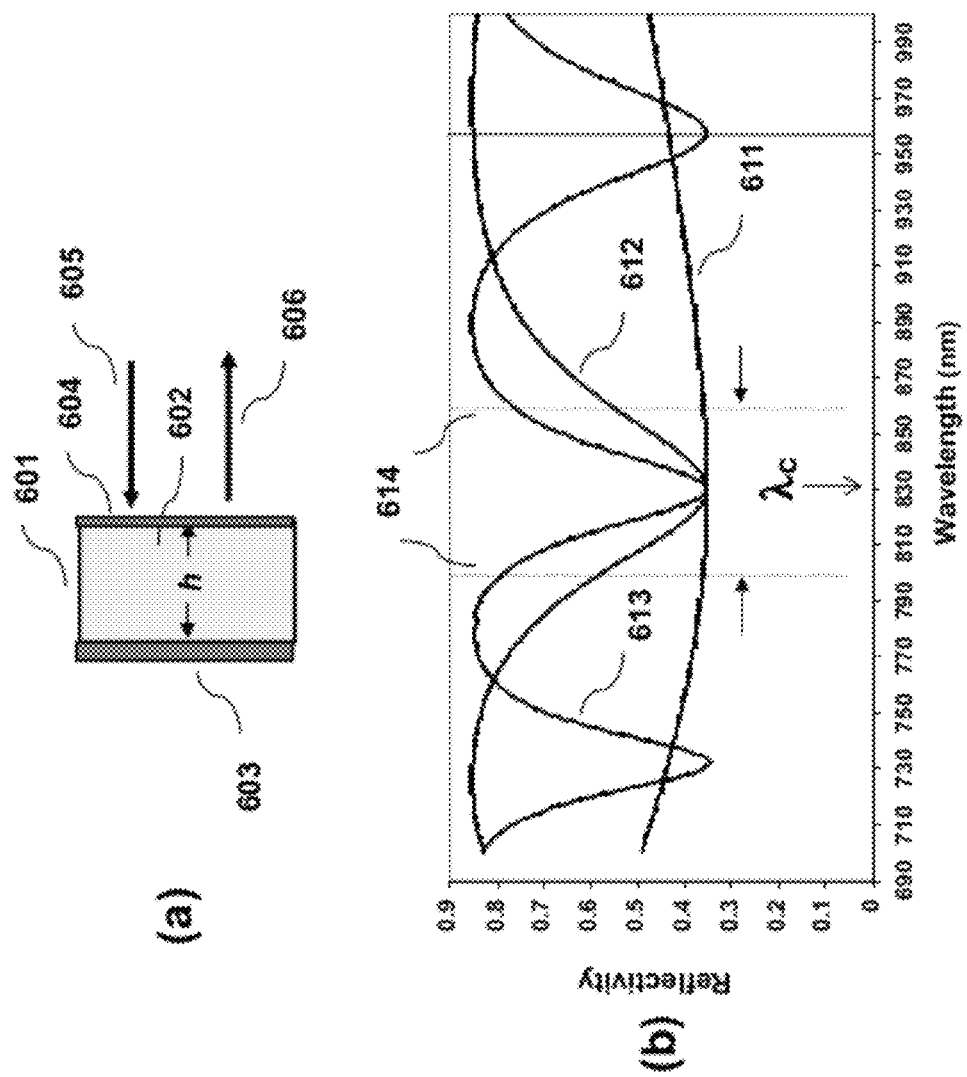
FIG. 6 shows:
(a) an exemplary back reflector design using multiple quarter-wave etalon for extending bandwidth of a discrete spectrum light source, and
(b) periodic reflectivity profiles for odd values of N showing increase in reflectivity coinciding with the band edges of the gain medium spectral profile as N increases.

In one embodiment of the invention raised-edge reflectivity is obtained by configuring an etalon as a back and/or a front reflector of a discrete spectrum source. By way of example, an etalon configured using a slab of material, preferably a dielectric material, with partially reflective parallel front and back surfaces is shown in FIG. 6. More specifically, in FIG. 6*a* is shown a basic etalon structure 601 having a dielectric material 602 of thickness 'h' disposed between a back reflector 603 and a front reflector 604. Light incident on one surface 605 undergoes multiple reflections from the reflective surfaces. These reflections add up in magnitude and phase and cumulative light 606 is output from the surface 604. In subsequent discussions the surface where the light is output will be referred to as the front reflective surface (or front reflector) and the opposite reflective surface will be referred to as the back reflective surface (or back reflector), respectively, unless mentioned otherwise.

For any given choice of etalon material, there is a maximum available contrast ratio that is determined by the mid-band reflectivity and maximum edge reflectivity. Therefore the maximum attainable contrast ratio depends on the choice of etalon material. However, any value of contrast ratio below the maximum can be obtained by the choice of etalon thickness. The higher the chosen mid-band reflectivity, the lower the maximum contrast ratio. For example, if the maximum reflectivity is 80% and the mid-band reflectivity is 40%, the maximum contrast would be 2.0. However the maximum contrast would be 8 if the mid-band reflectivity is 10%. Typically a stack etalon (one or more pairs of two materials having different refractive indexes) gives a higher contrast than a single-layer etalon. Regardless of the values of the reflectivity, the gain medium gain $Gs(\lambda)$ must be chosen such that the product $G_s(\lambda)\{R_1(\lambda)R_2(\lambda)\}^{1/2}$ (the cavity feedback factor K) is less than unity at all time.

It is well known in the art that output light from an etalon exhibits a periodic spectral profile showing maxima and minima as a function of wavelength. A maximum would occur at wavelengths for which the etalon thickness is an integer number of half wavelengths (halfwave layer) in reference to a selected center wavelength. A minimum would occur at the wavelengths for which the etalon thickness is an odd multiple of quarter wavelength (quarterwave layer) in reference to a selected center wavelength. It should be noted that while defining a quarterwave or a halfwave layer, the reference center wavelength is preferably the center wavelength of the gain medium spectrum unless otherwise specified. Therefore, in order for an etalon to exhibit a raised-edge reflectivity and a reflection minimum at a center wavelength of the gain medium, the etalon thickness must be an odd multiple of quarter wavelength. The actual value of these extrema (maxima and minima) is a function of the refractive index of the etalon dielectric material. Accordingly, the etalon material can be chosen to have a refractive index that satisfies the requirement for a desired back reflector or for a front anti-reflection (AR) layer.

Returning back to FIG. 6(a), an exemplary design for an etalon shown therein to be configured as an external back reflector having raised-edge reflectivity profile $R_1(\lambda)$ will be described next. The exemplary etalon 601 comprise a dielectric material 602 with refractive index $n_e$ and thickness h, placed between surfaces 603 and 604 having refractive indexes $n_r$ and $n_i$, respectively. Incident Light 605 entering from air to the etalon via the surface 604 undergoes multiple reflections in the etalon between the surfaces 603 and 604, and part of the light 606 is reflected back out of the surface 604. Selection of back and front reflector and arrows showing the direction of the incident and output light in this example merely describe the principle and are not to be construed as limiting.

An etalon configured in such a manner exhibits a reflection minimum at a center wavelength $\lambda_c$ and at other wavelengths if the thickness h of the etalon is an odd multiple of quarter-wavelengths in the etalon medium, i.e., $$h = N \frac{\lambda_c}{4 n_e}, \quad (8)$$

where $N = 1, 3, 5, \ldots$ is an odd integer.

Results of a calculated reflectivity profile for an etalon using $TiO_2$ having a refractive index $n_e$=2.49 disposed on an aluminum substrate, is shown in FIG. 6b. For the calculation, it is assumed that an exemplary SOA gain medium has a center wavelength at $\lambda_c$=830 nm, and light is incident from air on the etalon facet 604 (FIG. 6a). Reflectivity profiles for light reflected back from the etalon in the air for odd integers N=1, 7, and 15, respectively are shown as traces 611, 612 and 613, respectively, in FIG. 6b. More specifically, traces 611-613 show calculated reflectivity (y-axis) as a function of wavelength (x-axis). The trace 611 corresponds to N=1, for an etalon thickness of 83 nm which is practically flat between the dashed lines 614 at 800 nm and 860 nm representing the band edges where the intensity drops off by a factor of two. The space between the lines 614 represents the bandwidth of interest which is substantially flat (~34% at 830 nm and ~36% at the band edges) and overlaps with the bandwidth of a gain medium for example, a SOA gain medium of the discrete spectrum source (about 60 nm in this case). A contrast ratio C can be defined as the ratio of the reflectivity at one of the band edges to the reflectivity at mid-band, i.e., $$C = \frac{R_{BAND\text{-}EDGE}}{R_{MIDBAND}} \quad (9)$$

Using this criterion, for N=1 a contrast ratio of ~1.06 is obtained from the reflectivity profile shown in trace 611. Trace 612 corresponds to N=7 (etalon thickness 581 nm) and clearly shows a raised-edge profile with a contrast ratio C of 1.74 over the bandwidth of interest. Trace 613 corresponds to N=15 (etalon thickness 1,248 nm) revealing a raised-edge profile with a contrast ratio C of 2.34 over the bandwidth of interest. In addition, trace 613 exhibits two maxima of value 85% at 780 nm and 890 nm, respectively, and two other minima at 732 nm and 958 nm. However, for the purpose of bandwidth enhancement, additional maxima and minima are irrelevant because they are well outside the bandwidth of the gain medium. The spacing between adjacent minima or maxima is the "free spectral range" or FSR, and its value in the neighborhood of $\lambda_c$ is FSR=$2\lambda_c$/N. The maximum value of N is the value for which the FSR corresponds to the desired bandwidth. Thus $N_{MAX}$ is the odd integer that is nearest to the value $2\lambda_c$/B.

The etalon described in FIG. 6a is one example of a reflector with raised-edge reflectivity profile. Other suitable examples of raised-edge reflectivity profile reflector for application in a discrete spectrum source include, but are not limited to, pairs of multiple quarterwave layers comprising two materials having different refractive indexes, stacks of such pairs, stacks comprising pairs of odd multiple quarter-wave layers and pairs of multiple halfwave layers, Bragg gratings configured as double-pass reflectors, and other combinations that will be apparent to those skilled in the art. The examples given in this disclosure are merely to illustrate the principles and are not to be construed as limiting.

For illustrative purposes only and not as a limitation, a preferred embodiment of extended bandwidth source is assumed to have a gain medium comprising a SOA waveguide where gain of the medium is adjustable using any suitable means such as electrical or optical pumping. The discussion is equally pertinent to other gain media that includes but is not limited to, SLD, SOA, an ASE source, a solid state gain medium, a doped optical fiber. As has been disclosed in the co-pending U.S. patent application Ser. No. 13/111,047, content of which is incorporated by reference, a discrete spectrum source is configured by placing a SOA gain medium between a back and front reflector where the reflectivity of the back reflector is high and the reflectivity of the front reflector is preferably of the order of $10^{-5}$ to $10^{-6}$. It is also disclosed there that the SOA waveguide may include different waveguide structures for example, a tilted waveguide or a curved or a bent waveguide and the SOA waveguide may be tilted with respect to the front facet or it may be perpendicular to the front facet.

For this illustrative example, it is assumed that the back reflector has a raised-edge reflectivity as described in reference with FIGS. 5 and 6. The back reflector may be external to the gain medium or it may be deposited directly on the SOA waveguide facet. When the back reflector is external to the gain medium, the back facet of the gain medium must have very low reflectivity in order to avoid additional cavity effects in the overall structure. In this case, the SOA must be of the tilted waveguide type and the back facet of the SOA facing the external back reflector should be AR (anti-reflection) coated for low reflectivity. Such AR coating can easily reduce the back facet effective reflectivity to less than $10^{-7}$. These considerations lead to various design choices for reflectors. Some examples of preferred choices for back and front reflectors are shown in FIG. 7 and FIG. 8, respectively.

Figure 7:
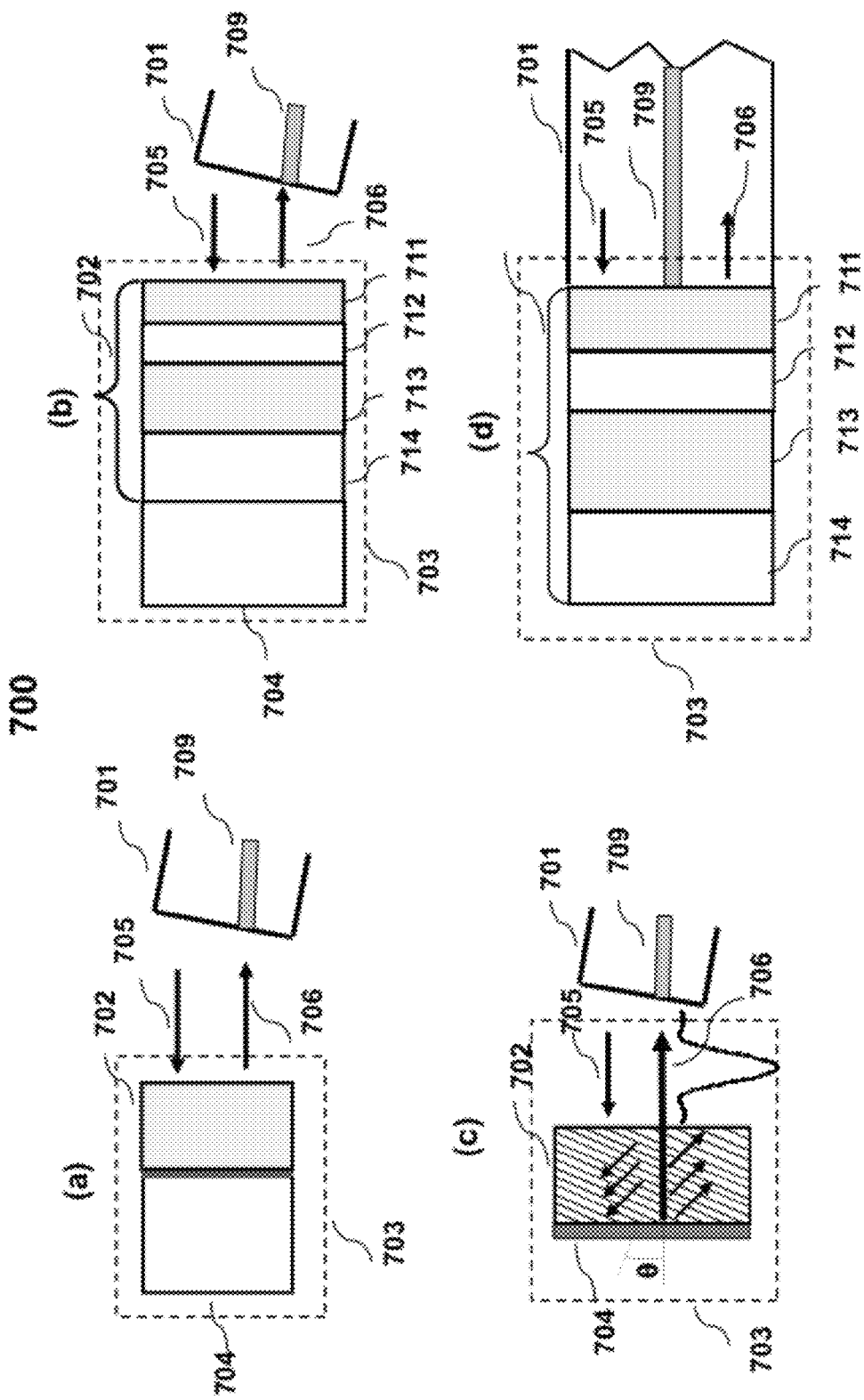
FIG. 7 shows exemplary configurations of back reflectors for an extended bandwidth discrete spectrum light source comprising:
(a) an external back reflector using a single etalon on a substrate,
(b) an external raised-edge reflectivity back reflector comprising a stack of multiple pairs of quarter-wave layers and multiple pairs of half-wave layers, using same two materials,
(c) a back reflector configured as a double-pass Bragg grating, and
(d) a raised-edge reflectivity back reflector applied directly to the back facet of a discrete spectrum light source with waveguide perpendicular to the back facet.
Figure 8:
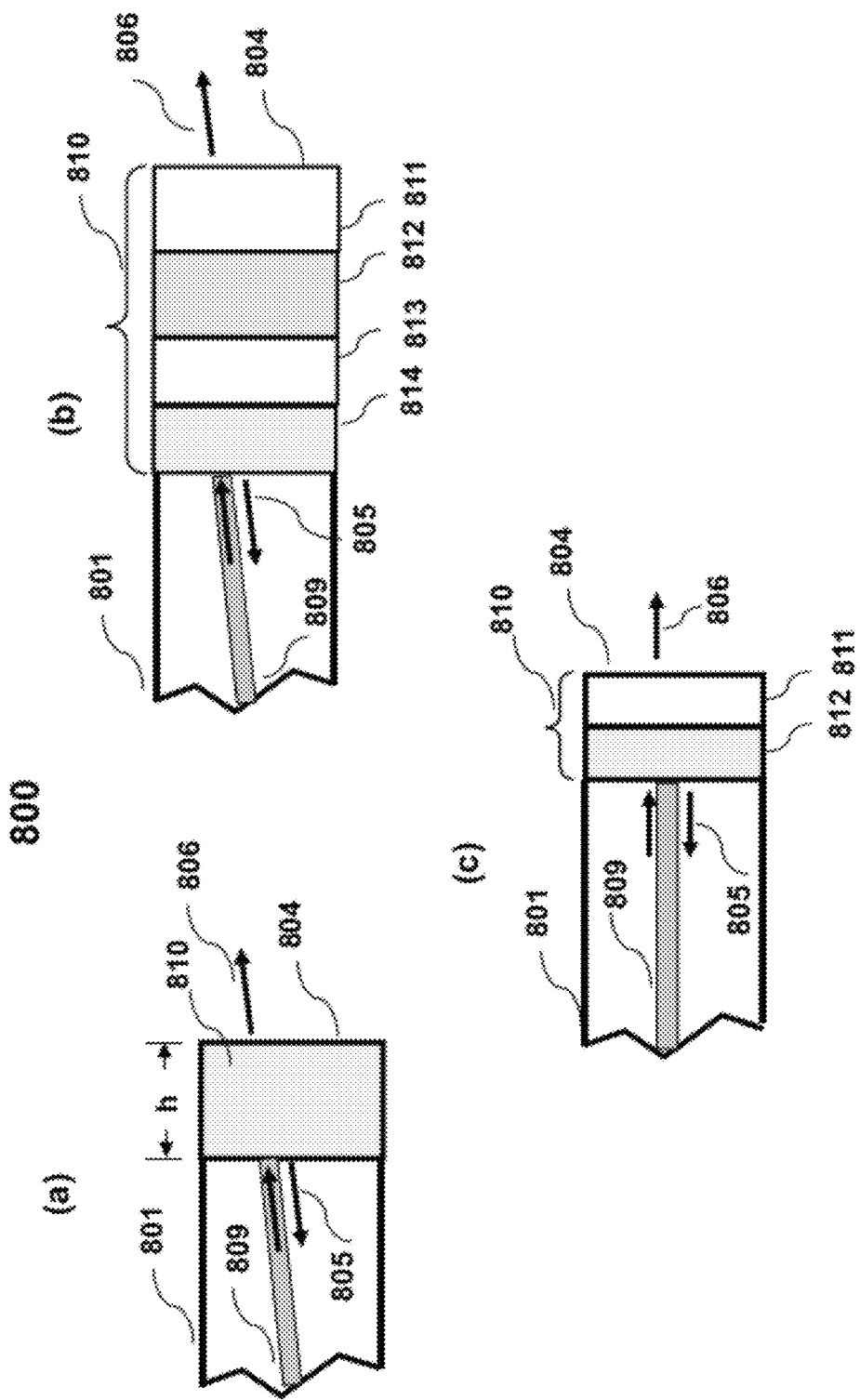
FIG. 8 shows exemplary configurations of raised-edge low reflectivity front reflector comprising:
(a) single multiple quarter-wave etalon directly deposited on the front facet of an SOA with tilted waveguide,
(b) stack reflector directly deposited on the front facet of an SOA with tilted waveguide, and
(c) special design of a high raised-edge reflectivity contrast obtained by stacking two thin layers of two different materials to approximate the ideal quarter-wave AR coating on an SOA front facet.

In FIG. 7, a schematic view 700 shows examples of back reflector design suitable for an extended bandwidth discrete light source featuring a tilted waveguide SOA or a bent waveguide SOA. SOA gain medium in the examples shown here is selected to illustrate the principles of this invention and is not to be construed as limiting. Other variations of gain medium within the framework of this invention that may occur to those skilled in the art are not precluded. Referring simultaneously to prior art FIG. 2a and FIG. 7, each example in the schematic view 700 (a-d) shows a dashed rectangle 703 which represents the back reflector 203 in the discrete spectrum source design shown in FIG. 2a. And while the detail configuration in each example may vary, the functionality is identical. Bold arrows indicate the direction in which light travels inside and outside the gain medium. They are shown for illustrative purpose with respect to the configurations shown in FIG. 7, and are not to be construed as limiting.

The back reflectors shown in examples 700 'a-c' are disposed on a highly reflective substrate 704. By way of example, said reflective surface is either a highly reflective metallic surface or a non-reflective surface coated with a highly reflective metallic layer. An etalon 702 is configured as a back reflector with raised-edge reflectivity profile for a gain medium 701 comprising a tilted waveguide SOA 709. In the example shown in 700 'd' the waveguide is perpendicular to an end facet. The etalon sections 702 of the reflectors are configured either as a single layer (a) or as a stack (b-d); each specific example will be described shortly.

Tables BR1-BR4 below, lists reflectivity and contrast ratio numbers obtained for different etalon design according to the principles outlined earlier. In Table BR1, BR2 and BR4, the first column lists the etalon material, the second column lists the etalon thickness (in terms of odd integers N of the quarter wavelengths), the third column lists the reflectivity values at the desired center wavelength (830 nm in this example), and the fourth column lists the contrast ratio.

More specifically, a first exemplary back reflector embodiment represented in the schematic 700 'a' is a single layer etalon reflector comprising a titanium dioxide (TIO$_2$), germanium (Ge), or silicon (Si) layer having an effective refractive index $n_r$, disposed on a substrate coated with an aluminum reflective layer. Reflectivity and contrast ratios obtained for the three different single layer etalon reflectors are listed in Table BR1 to highlight that by appropriately selecting etalon materials and their respective thicknesses different reflectivity and edge contrast ratio can be obtained.

TABLE BR1

Single Etalon External Back Reflector on Aluminum Substrate

| Etalon | N | R (center) | Contrast ratio |
|---|---|---|---|
| TiO$_2$ | 1 | 34.00% | 1.06 |
| | 7 | | 1.74 |
| | 15 | | 2.34 |
| Germanium | 3 | 6.50% | 4.1 |
| | 5 | | 7.3 |
| | 7 | | 9.4 |
| Silicon | 5 | 17.50% | 2.7 |
| | 7 | | 3.4 |

In an alternative embodiment it may be preferable to deposit the etalon layer directly on a substrate such as germanium or gallium arsenide (GaAs) without the aluminum backing layer. Reflectivity and contrast ratio numbers comparable to those obtained with the aluminum backing layer are achieved if the etalon is constructed in form of a stack as shown in the schematic 700 'b' and 'd' in FIG. 7, respectively. A simple stack comprise of a pair of materials having different refractive indexes. Such pairs include but are not limited to, silicon dioxide (SiO$_2$) and silicon, titanium dioxide, germanium, etc. for example, SiO$_2$/TiO$_2$, SiO$_2$/Ge, or SiO$_2$/Si, etc. The layer thicknesses may be odd integer multiples of quarter wavelength as per Eq. (8), or integer multiples of half wavelength (N$\lambda_c$/2n$_e$), where n$_e$ is the refractive index of the particular layer).

A multiple stack would consist of several such pairs. Normally, the reflectivity exhibits a maximum at the center wavelength if all the layers are of quarter wavelength thickness, which is not a desirable option for configuring a back reflector according to this invention. However, a minimum at the center is obtained if the stack consists of one pair of quarterwave layers 711 and 712 and one pair of halfwave layers 713 and 714 as shown in 700 'b' and 'd' for an all-dielectric (no metal) external back reflector that exhibits raised-edge reflectivity featuring a tilted waveguide SOA for the gain medium in 'b' and a perpendicular waveguide in 'd'. Table BR2 shows some results of exemplary configurations in which the substrate is Ge and GaAs, respectively for an external back reflector.

TABLE BR2

Four-Layer Quarterwave-Halfwave External Back Reflector Pair on Ge Substrate

| Pair | N | R (center) | Contrast ratio |
|---|---|---|---|
| SiO$_2$/TiO$_2$ | 3 | 5.40% | 3.7 |
| | 5 | | 6.8 |
| | 7 | | 8.5 |

Four-Layer Quarterwave-Halfwave External Back Reflector Pair on GaAs Substrate

| Pair | N | R (center) | Contrast |
|---|---|---|---|
| SiO$_2$/Ge | 5 | 24.10% | 2.38 |
| | 7 | | 3.14 |

In another embodiment of an external back reflector a Bragg grating disposed on a highly reflective substrate or surface having a highly reflective coating may be as effective. An example of such a configuration is shown in the schematic view 700 'c' in FIG. 7. A grating comprises a "periodic structure" consisting of alternate regions of slightly different refractive indexes. A simple Bragg grating is made by a holographic method on a photosensitive medium, followed by developing and fixing. This is a well known process and will not be described here. For the purpose of this invention, the grating is represented as a series of slats at a specific angle θ, known as the Bragg angle, with respect to the incident light.

Theoretically, depending on the strength of the index differences and the thickness of the grating, part of the incident light is diffracted into a so-called $1^{st}$ order, and the undiffracted component, called the $0^{th}$ order propagates through the grating. In this case, the $0^{th}$ order is reflected and undergoes additional diffraction. The result is that the net reflection is what is left of the $0^{th}$ order in its double pass through the grating. The bandwidth of the diffraction is determined by the index step and the grating thickness.

Table BR3 shows results for exemplary grating designs 1, 2 and 3 for three different values of mid-band reflectivity and contrast ratio. Column 1 in Table BR3 lists the grating parameters and columns 2, 3 and 4 show the numerical value of that parameter for a particular design. More specifically, the grating parameters are, material refractive index, index steps, grating periods, thicknesses and grating Bragg angles. The last two rows show the reflectivity at the center wavelength and the contrast ratio for three different grating designs. The parameters listed in Table BR3 are merely meant to be examples to describe the principle of the invention and are not to be construed as limiting.

TABLE BR3

Double-Pass Grating Reflector on Aluminum Substrate

| | Design Serial Number | | |
|---|---|---|---|
| | 1 | 2 | 3 |
| Material refractive index | 1.6 | 1.6 | 1.6 |
| Index step | 0.005 | 0.006 | 0.005 |
| Grating period (nm) | 528 | 590 | 530 |
| Thickness (microns) | 32 | 34 | 32 |
| Grating angle (deg.) | 27.13 | 25.25 | 27.8 |
| R (center) (%) | 33 | 17 | 10 |
| Contrast ratio | 3 | 5.9 | 5.8 |

In the embodiments described earlier, the back reflector is external to the gain medium comprising a tilted-waveguide SOA. Extended bandwidth source may also be configured where the back reflector is deposited on the back facet of the gain medium or the SOA waveguide, as shown in the schematic view 700 'd' in FIG. 7. This option is particularly useful in a configuration where the waveguide is perpendicular to the back facet (not tilted). Due to the high refractive index of the SOA material (about 3.34), a single-layer etalon does not provide a good contrast ration in a raised-edge reflectivity profile. However, a combination of quarterwave layer and halfwave layer pairs, as shown in the view 700 'd' provides a comparable reflectivity and excellent contrast ratio. The results for stacks of $Si/SiO_2$ pair (multi-quarterwave pairs followed by multi-halfwave pairs) and $Ge/Al_2O_3$ pairs are shown in Table BR4.

TABLE BR4

Four-Layer Stack Quarterwave-Halfwave
Reflector Pair Directly on SOA's Back Facet

| Pair | N | Rcenter | Contrast |
|---|---|---|---|
| Si/SiO2 | 3 | 9.30% | 6.1 |
| | 5 | | 7.7 |
| Ge/Al2O3 | 3 | 15.10% | 4.8 |
| | 5 | | 5.5 |

For designing a front reflector having a raised-edge reflectivity, it is important to recall from the co-pending U.S. patent application Ser. No. 13/111,047, that the reflectivity number must be several orders of magnitude lower than the back reflector reflectivity. There it is disclosed, that a reflectivity of the order of $10^{-5}$ to $10^{-6}$ is preferable for the front reflector for a discrete spectrum source. When the gain medium is a tilted waveguide, basic low reflection is provided by the tilt (about $2.5 \times 10^{-5}$ reflection for a 6 degree tilt angle). Therefore it is sufficient to deposit an antireflection (AR) layer or a stack on the front facet to reduce the net front reflection to the desired minimum and provide the desired raised-edge reflectivity. FIG. 8 represents different designs for providing a raised-edge reflectivity for a front reflector of a discrete spectrum source configured using a tilted-waveguide SOA. And while this example is described using a SOA, by applying the same design principles, the feedback cavity design can be suitably adapted to other gain media.

In particular, in FIG. 8 is shown a schematic view 800 representing three different AR coating designs 'a-c', for obtaining raised-edge low reflectivity suitable for a front reflector application in an extended bandwidth discrete spectrum source. The schematic view 800 'a' shows a front reflector design with a single etalon layer 810 comprising a plurality of quarterwave layers deposited on the facet 804 of the gain medium 801 comprising a tilted waveguide SOA 809. The bold arrows indicate the directions of the input and output light 805 and 806 respectively. The antireflection coating functions as a low reflectivity reflector having a raised-edge reflectivity profile.

Some representative design options according to this invention are listed in Tables FR1-FR3 and the parameters listed therein have same general meaning as the parameters listed in Tables BR1, BR2 and BR4 in reference with the back reflector design described earlier and will not be described again. Notably, the reflectivity R(center), at a selected center wavelength (830 nm for this illustrative example) in Tables FR1-FR3 are much lower than those listed in Tables BR1-BR4.

Table FR1 below lists $SiO_2$, $TiO_2$, and $Al_2O_3$ etalons for an extended bandwidth discrete spectrum source using a tilted waveguide SOA as the gain medium for illustrative purpose. Notably, the $Al_2O_3$ etalon with N=1, is not desirable for a raised-edge front reflector because of its low contrast. However, it has one order of magnitude lower reflectance and a flat profile (contrast ratio ~1.17 which makes it suitable for back facet AR coating for configuring a discrete spectrum source using a tilted waveguide SOA in a cavity reflector with an external back reflector.

TABLE FR1

Single Quarterwave Etalon Layer on
Tilted SOA Facet

| Etalon | N | R (center) | Contrast ratio |
|---|---|---|---|
| SiO2 | 11 | 1.15E−06 | 3.32 |
| | 15 | | 4.55 |
| TiO2 | 19 | 2.25E−06 | 2.9 |
| Al2O3 | 11 | 2.00E−07 | 16.5 |
| | 1 | | 1.17 |

To configure a front reflector having a higher contrast ratio a quarterwave/halfwave layer multi-stack described in reference with the back reflector design, is more suitable instead of a single layer etalon. In the schematic view 800 'b' the etalon region collectively shown as 810, comprising multiple layers 811-814 is directly deposited on the waveguide facet. Rest of the source is similar to the source configured using a tilted-waveguide SOA gain medium, shown in the schematic view 800a for a single layer etalon configuration. Some exemplary etalon systems are summarized in Table FR2 for illustrative purposes and it is not to be construed as limiting to only these systems.

TABLE FR2

Four-Layer Stack Quarterwave-Halfwave
AR on Tilted SOA's Back Facet

| Pair | N | R (center) | Contrast ratio |
|---|---|---|---|
| Si/SiO2 | 5 | 2.30E−06 | 7.7 |
| Si/Al2O3 | 5 | 8.60E−07 | 19.6 |
| Ge/SiO2 | 5 | 6.00E−06 | 3.53 |
| Ge/Al2O3 | 5 | 3.80E−06 | 5.45 |
| TiO2/SiO2 | 5 | 1.44E−07 | 53.4 |
| TiO2/SiO2 | 1 | 1.44E−07 | 4.51 |

A special situation occurs when a waveguide is perpendicular to the front facet. In this case, it is not possible for an AR coating to provide a sufficiently low reflectivity. However, from a theoretical consideration, it is possible to achieve extremely low reflectivity together with very high raised-edge contrast ratio with a single quarterwave layer if the refractive index $n_e$ of the quarterwave layer is the geometric mean of the refractive indexes of the input medium and the output medium (the square root of their product). For example, if an input medium refractive index is $n_s$ and an output medium refractive index is $n_3$, the minimum reflectance will be close to zero over a narrow range if the value of the refractive index of the quarterwave layer is $\sim(n_s.n_3)^{1/2}$.

In FIG. 8, schematic view 800 'c' shows an embodiment where 801 is a SOA gain medium having refractive index $n_s$. Unlike the configurations shown in schematic views 800 'a' and 'b', the waveguide 809 in this configuration is perpendicular to the front facet 804. The output light 806 traverses in an output medium having a refractive index $n_3$. In order to achieve a raised-edge reflectivity profile for the quarterwave layer collectively shown as 810, the required refractive index value must be $n_e = (n_s n_3)^{1/2} = 1.83$ if $n_s$ is 3.34 and $n_3 = 1$ (refractive index of air in this illustrative example).

A material having a refractive index of 1.83 is not known in the art. However, a very good approximation to that value can be obtained by creating a composite layer structure consisting of very thin layers (thinner than a quarter wave) of two materials, one with refractive index lower than 1.83, such as $SiO_2$ having a refractive index ~1.47 and the other with a higher refractive index than 1.83, such as TaO having a refractive index 2.057. In general, if $n_1$ is the refractive index of the first material and $h_1$ is its thickness, and $n_2$ is the index of the second material and $h_2$ is its thickness, then the effective refractive index of a two-layer composite is an average value given by—

$$n_e = \sqrt{\frac{h_1 n_1^2 + h_2 n_2^2}{h_1 + h_2}} \quad (10)$$

Various combinations of $h_1$ and $h_2$ can be used to achieve a desired reflectivity and effective index of value between $n_1$ and $n_2$, including the target value, over a narrow range. For consistency, we use the notation $h_1 = N_1 \lambda_c / 4n_1$, and $h_2 = N_2 \lambda_c / 4n_2$, where $N_1$ and $N_2$ are small fractions. Accordingly, exemplary etalon using TaO/SiO2 pair may be designed using parameters listed in Table FR3. More specifically, for an exemplary gain medium having $\lambda_c = 830$ nm, $N_1$ and $N_2$ in the range 0.13 to 0.18, respectively, $n_1 = 1.47$ and $n_2 = 2.057$, $\lambda_c / 4n_1 = 141.16$ nm and $\lambda_c / 4n_2 = 100.88$ nm would result in $h_1$ and $h_2$ values listed in columns 2 and 4, respectively. Reflectivity (at $\lambda_c = 830$ nm) and band edge-mid-band contrast ratio for these set of parameters are listed in columns 5 and 6, respectively.

TABLE FR3

TaO/SiO$_2$ pair as Matching Index on SOA Without Tilt

| $N_1$ | $h_1$ (nm) | $N_2$ | $h_2$ (nm) | R (center) | Contrast Ratio |
|---|---|---|---|---|---|
| 0.178 | 25.13 | 0.136 | 13.72 | 5.50E−06 | 163 |
| 0.1778 | 25.10 | 0.1367 | 13.79 | 1.07E−05 | 93 |
| 0.1770 | 24.99 | 0.1372 | 13.84 | 2.13E−05 | 43 |
| 0.1760 | 24.84 | 0.1385 | 13.97 | 4.8E−05 | 19.6 |

Figure 9:
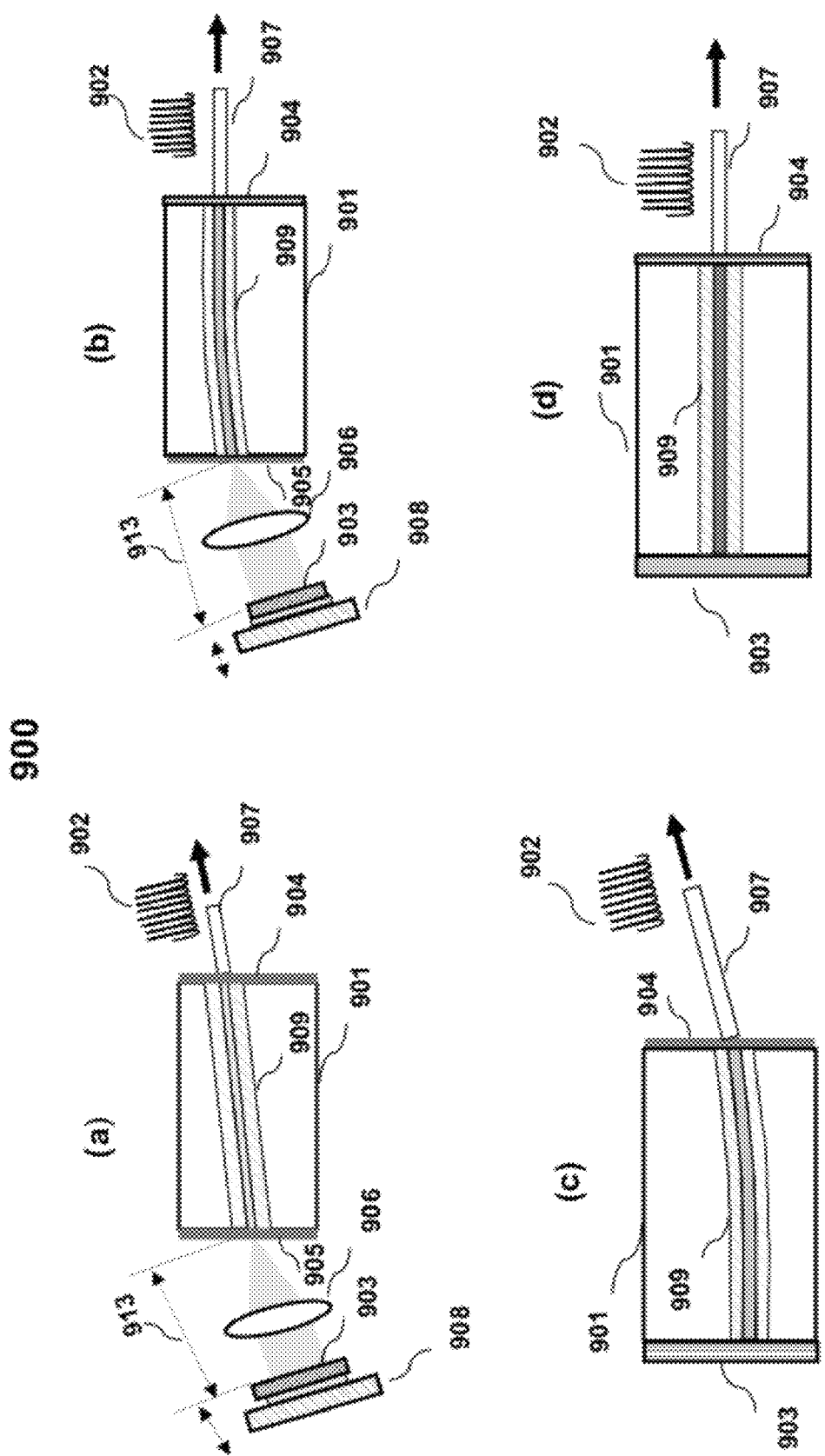
FIG. 9 shows exemplary configurations of extended bandwidth discrete spectrum light source comprising:
(a) an external cavity including raised-edge reflectivity back and front reflectors with a tilted waveguide gain medium,
(b) an external cavity including a raised-edge reflectivity back reflector and a composite refractive index matching pair front reflector with a bent waveguide gain medium with the tilt at the back facet,
(c) a cavity with raised-edge reflectivity front and back reflectors constructed on the facets of a tilted waveguide gain medium with the tilt at the front facet, and
(d) a cavity with raised-edge reflectivity back reflector and a composite index matching pair front reflector constructed on the facets of a bent waveguide gain medium perpendicular to the facets.

Preferred embodiments of extended bandwidth discrete spectrum source are shown in FIG. 9, where bandwidth expansion is achieved by configuring the feedback cavity having raised-edge reflectivity described in reference with FIGS. 7 and 8 and their properties summarized in Tables BR1-BR4 and Tables FR1-FR3, respectively. In embodiments of the extended bandwidth sources to be described shortly, the feedback cavity is either external to the gain medium or is directly disposed on the gain medium facet(s), or a combination thereof. In embodiments where an external back reflector is used, additional single quarterwave layer antireflection (AR) coating is disposed at the back facet of the gain medium for further reflectivity reduction such that, the reflectivity of the front reflector is several orders of magnitude lower than the reflectivity of the external back reflector without additional cavity effects arising due to high reflectivity of the back facet of the gain medium.

Exemplary configurations of extended bandwidth source are shown in schematic views 900. More specifically, to extend the bandwidth of a discrete spectrum source a gain medium 901 is placed in a feedback cavity comprising a back reflector 903 and a front reflector 904, respectively. The gain medium includes but is not limited to, SLD, SOA, an ASE source, a solid state gain medium or a doped optical fiber, where gain of the medium is adjustable by a suitable external means, such as electrical or optical pumping. In the example shown in FIG. 9, the gain medium comprises a waveguide structure 909 which in the exemplary configurations, are shown to be straight, tilted, bent or curved with respect to the respective facet(s). As shown in FIG. 9 (a)-(d), front and/or back end of the waveguide may be perpendicular or at an angle with respect to a respective end facet.

In the configurations using an external feedback cavity the back reflector is shown to be mounted on a translation device 908, such that the distance between the back facet of the gain medium and the back reflector 913, can be adjusted to vary the pitch (spatial distribution) of the discrete emission lines 902. One advantage of an external back reflector is that the emission lines are made to match with the pitch of the detector array for allowing maximum optical power to impinge on the detector. The feedback cavity design is similar to that described in reference with the prior art devices shown in FIGS. 2a and 2b, respectively, except that the external back reflector 903 and the front facet AR coating 904 have raised-edge reflectivity, while the back facet 905 of the SOA gain medium is coated with a very low reflectivity AR coating having a flat-profile.

Specific embodiments of the invention will be described now to illustrate how different design elements described earlier may be suitably combined to construct feedback cavity of an extended bandwidth discrete spectrum source. The selected examples are merely for illustrative purpose and are not to be construed as limiting. Referring now to a particular embodiment 900 'a', the extended bandwidth source comprising a tilted waveguide SOA gain medium where the waveguide ends are tilted at the front and back facets, is disposed in an external feedback cavity comprising an external back reflector 903. The back and front reflectors having raised-edge reflectivity may be constructed using any of the designs shown in FIGS. 7 and 8, respectively. Different feedback cavities may be constructed using the parameters listed in Tables BR1, BR2, or BR3, and Tables FR1 or FR2, for back and front reflectors, respectively.

For example, a desired reflectivity for the back reflector at the mid-band of the SOA gain spectrum is selected first such that it is several orders of magnitude higher than the minimum reflectivity of the front reflector (at the mid-band of the SOA gain spectrum). Since the maximum reflectivity at any wavelength can never be more than 100%, the available contrast is higher for a lower minimum reflectivity. For example, with a 6-degree tilt angle for the gain medium waveguide, front facet reflectivity is about $2.5 \times 10^{-5}$ at all wavelengths and an etalon or stack AR coating described earlier, is necessary to lower it further and raise the spectrum at the SOA band edges.

Front reflector may be designed by using parameters in Tables FR1 and FR2 to provide minimum reflectivity between $10^{-5}$ and $10^{-6}$ with adequate raised edges. The back SOA facet should ideally be without reflection at all wavelengths, but it is not possible without a suitable AR coating. A very low flat spectrum reflection can be obtained on the back facet surface by applying a single quarterwave $Al_2O_3$ layer (N=1 as in Table FR1) which, together with the tilted configuration gives an effective reflectivity of $2.0 \times 10^{-7}$ with a contrast of only 1.17.

An alternative embodiment shown in schematic 900 'b' comprises a curved waveguide SOA gain medium having a tilted back end and a perpendicular front end with respect to facets 905 and 904, respectively. The tilt at the back facet makes this configuration suitable for a source with an external back reflector. This embodiment is similar to the prior art discrete spectrum source shown in FIG. 2b except that the external back reflector is constructed to have raised-edge reflectivity. More specifically, a suitable back reflector for the external cavity may be constructed by using reflector parameters listed in any of the Tables BR1, BR2, or BR3. In this example the front end of the waveguide is perpendicular to the gain medium facet. One option for a suitable front facet AR coating may be a matching refractive index layer structure shown in FIG. 8 'c' for which design parameters are listed in Table FR3.

More specifically, an AR coating for near zero reflection over a narrow range may be constructed using a single quarterwave layer with a refractive index that is the geometric mean of the indexes of the two regions to be matched. For matching refractive index of an SOA gain medium to the outside air, an AR coating of refractive index of about 1.83 may be achieved by a stack of thin layers of silicon dioxide ($SiO_2$ or ordinary glass) and tantalum oxide (TaO) as disclosed in Table FR3. For example, for a reflectivity of about $10^{-5}$ with a contrast ratio of 93, 82.9 nm $SiO_2$ layer and 71.74 nm TaO layers are suitable. Notably, the thickness of each of the layers is preferably 100 nm or less.

Another embodiment featuring a curved waveguide SOA gain medium is shown in the schematic view 900 'c'. However, the perpendicular side of the waveguide is at the back facet and the tilted side is at the front facet. In this configuration, the extended bandwidth discrete source does not require an external back reflector for the feedback cavity. Instead, the raised-profile back reflector is directly deposited on the back facet of the SOA gain medium. For the back reflector an etalon comprising multiple quarterwave layers or a combination of multiple quarterwave and multiple halfwave layers of the same two materials, shown in FIG. 7 (700 'd') are equally applicable. However, for more choices of minimum reflectivity and contrast ratio values, the latter choice is preferable for which parameters are listed in Table BR4. Since the waveguide end in the front is tilted, a front facet reflector may be constructed using a design shown in FIG. 8 (800 'a' and 'b') for which design parameters are listed in Tables FR1 or FR2.

A preferred embodiment featuring a straight waveguide gain medium typically used for semiconductor lasers, is shown in FIG. 9 (900 'd'). Normally, a straight waveguide gain medium is not considered suitable for a broadband emission device. However, combined with the principles of this invention, it is possible to construct an extended bandwidth discrete spectrum source by placing a straight waveguide gain medium in a feedback cavity using raised-edge reflectivity back and front reflectors described earlier. Accordingly, a back reflector is configured using a stack reflector design shown in FIG. 7 (700 'd'). Design parameters listed in Table BR4 are suitable to construct a multiple stack of quarterwave and halfwave layers for achieving a desired raised-edge reflectivity with a good contrast ratio. For the front facet, an AR coating similar to that shown in FIG. 8 (800 'c') is most suitable for a straight waveguide gain medium. Design parameters listed in Table FR3 can yield very low minimum reflectivity ($10^{-5}$ to $10^{-6}$) with very high contrast ratio.

Advantageously, the waveguide structure is similar to that of a semiconductor laser and technology for constructing semiconductor lasers and applying AR coating to laser facets is quite well known and well developed in the art. Therefore the embodiment using a straight waveguide laser gain medium and applying raised-edge reflectivity reflectors to the facets directly, to construct an extended bandwidth discrete spectrum source is readily adaptable and cost effective for mass production.

Bandwidth Enhancement—Signal Processing Method:

The previous section discussed bandwidth enhancement for a discrete spectrum source by configuring a gain medium in a feedback cavity where the front and back reflectors of the cavity exhibit a raised-edge reflectivity. A gain medium placed in such a reflector cavity results in a source with enhanced bandwidth over a prior art discrete spectrum source configured using reflectors having a flat reflectivity spectra. Further enhancement in bandwidth can be achieved by implementing signal processing tools at a system level after a spectral component of interference signals in a OCT system is detected in the detector array of the OCT system. At the system level, bandwidth enhancement is achieved by digitally applying arithmetic operation(s) to signals detected at the detector elements near the band edges using signal processing tools that are well known in the art.

More specifically, in a SD-OCT imaging system, each detector array element receives an interference signal and produces an electric current or a voltage proportional to the light intensity impinging on the detector element at the specific wavelength corresponding to the detector element. A sequential readout of these individual signal elements produces a digital spectrum of the interference signal in the frequency (more specifically the wavelength) domain. The bandwidth of the interference signal spectrum is the same as the source bandwidth. It is desirable to enhance the bandwidth further to maximum possible extent so that an image generated from the collective interference signal has better depth resolution. One option to achieve additional bandwidth enhancement is to scale up the magnitude of the weaker detected components of the interference signal that are around and beyond the half-power points of the detected spectrum. The scaling can be achieved by applying an arithmetic operation (addition or multiplication) to the detected interference signal.

As an example, the detected signal is multiplied preferably by a predetermined factor at each detector, such that the signal-to-noise ratio (SNR) is not lowered beyond a certain minimum acceptable limit. For example, if a minimum SNR of 20 dB is considered adequate and if the SNR of a signal component at a point beyond the half-power points is 26 dB, then an enhancement by a factor of up to 4 is acceptable to maintain the SNR within the 20 dB limit. Enhancing the bandwidth at the post-detection level requires signal processing tools including a digital compensation function that peaks around the band edges. The digital compensation function when multiplied one-on-one with the detected signal components boosts the weaker signals at the band edges during the simultaneous readout of the detector signals into the Fourier Transform (FT) device. The digital compensation operation just described, preferentially increases the amplitude of the band edge elements relative to those at mid-band, thus advantageously provide further bandwidth enhancements at the system level over what is already obtained by the extended bandwidth discrete spectrum source described earlier.

Figure 10:
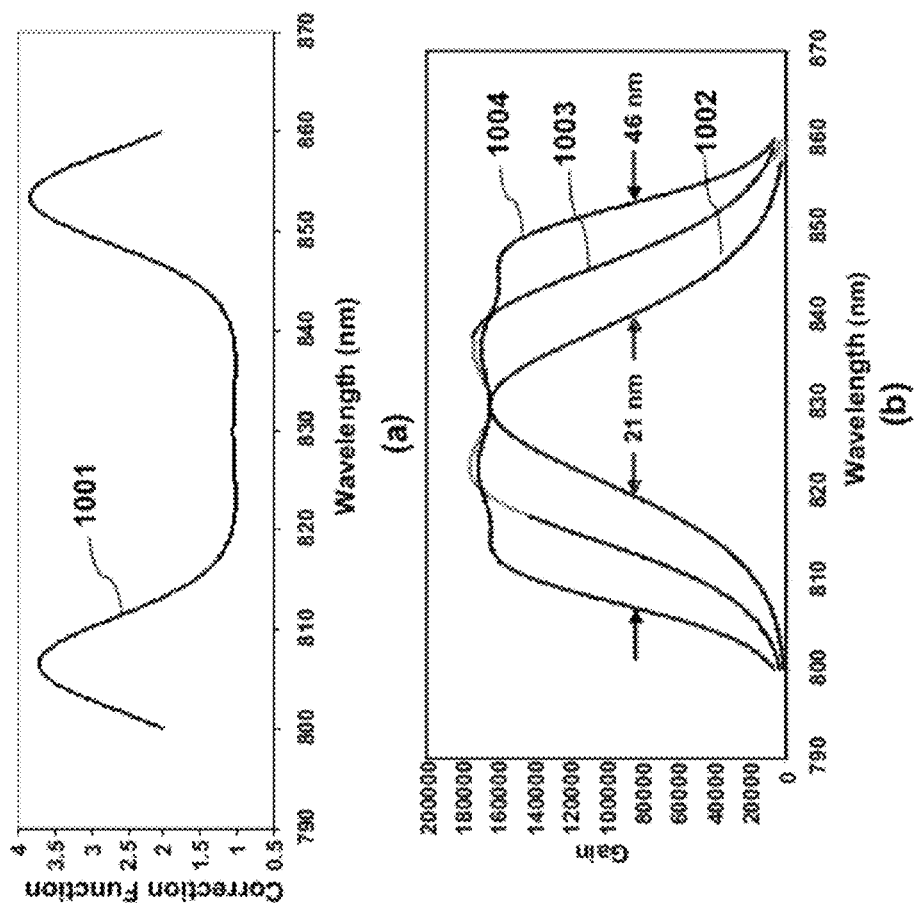
FIG. 10 shows:
(a) an exemplary profile of a function which when multiplied with the detector signal elements would enhance the overall bandwidth of a system configured with a extended bandwidth discrete spectrum light source, and
(b) overall bandwidth enhancement of a discrete spectrum light source configured with raised-edge reflectors in conjunction with post-detection signal processing.

The multiplication process does not significantly deteriorate the SNR because it operates on both the signal and noise components. An example of a digital multiplier function $P_m$ is shown in FIG. 10a for the exemplary spectral profile of the extended bandwidth source described earlier in reference with FIG. 5b (trace 504). More specifically, the function 1001 is a digitally generated function showing compensation value (y-axis) as a function of wavelength (x-axis). The compensation function is obtained by first determining the broadest spectral profile $P_f$ within the SNR specifications and then dividing it (element by element) by the source spectral profile which is the same as the detector profile $P_d$ (i.e., $P_m = P_f/P_d$), and storing the digital components of $P_m$ in the system's memory. The compensation function 1001 has peaks at the band edges where the intensity of the extended bandwidth source is expected to fall off. After the digital interference data is read into the processor, software tools are used to read each signal component and fetch the corresponding multiplier element before feeding the new values to the FT device circuit.

Referring simultaneously to FIGS. 5b and 10b, an exemplary final spectrum resulting from the signal processing operation performed on the exemplary extended bandwidth source described in reference with FIG. 5b is shown in FIG. 10b. More specifically, the graph shown in FIG. 10b includes three traces 1002-1004. Trace 1002 represents a spectral profile of a prior art discrete spectrum source with a feedback cavity configured using flat reflectivity reflectors exhibiting a half-power bandwidth of ~21 nm. Trace 1003 represents a spectral profile for an extended bandwidth source having ~34 nm bandwidth, configured using a feedback cavity having raised-edge reflectivity reflectors described in this application. A bandwidth enhancement of about 13 nm is achieved. Trace 1004 obtained after post-detection signal processing exhibits a bandwidth of ~46 nm.

An overall bandwidth enhancement by a factor of 2 or more is achieved over the prior art discrete spectrum source by applying new feedback cavity design and the post-detection signal processing method. It can be well appreciated that the bandwidth enhancement thus obtained results in improving the resolution from 14.4 microns to 6.6 microns which could only be obtained by staggering at least two carefully matched prior art sources. By carefully selecting design parameters such as, gain medium bandwidth, reflectivity and edge-midband contrast ratio values for the back and front reflectors bandwidth may be optimized for providing an overall resolution of the order of 3 microns. A further bandwidth reduction below 3 microns may be achieved by staggering two or more extended bandwidth sources.

Advantageously, by applying digital correction to the detected signal at the system level, the spectral profile of the detected signals may be modified to obtain a desired shape that would be free of spectral side bands and therefore free of imaging artifacts. For example, a Gaussian profile is ideal to avoid sidebands generation. Therefore, the function $P_f$ may be selected to be a Gaussian function, and the digital components of the compensating function $P_m$ derived accordingly. The detected interference signal spectrum is therefore converted to have a Gaussian profile after applying a suitable correction. The image quality may thus be improved by removing sidebands almost completely.

Figure 11:
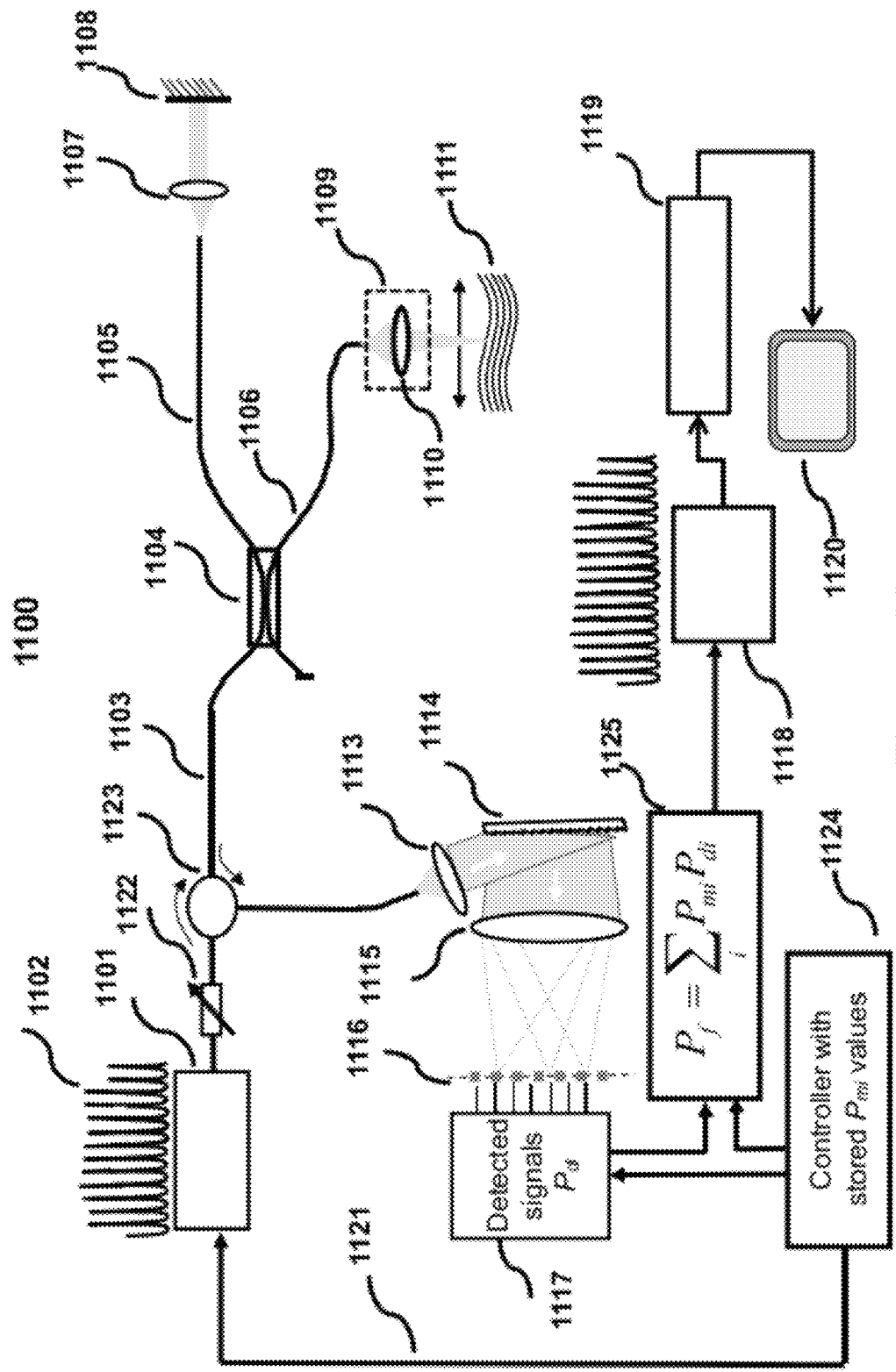
FIG. 11 shows a schematic representation of an exemplary OCT system configured in SD-mode using an extended bandwidth discrete spectrum light source and a processor to apply post-detection signal processing for additional bandwidth enhancement.

FIG. 11 schematically shows an SD-OCT system 1100 incorporating an extended bandwidth source as well as additional signal processing capability for bandwidth enhancement. The system 1100 described here is similar to the prior art SD-OCT system shown in FIG. 1 in design and its basic operation except, it includes an extended bandwidth source 1101 and signal processing functions 1124 and 1125 in a processor unit to perform post-detection bandwidth enhancement in software according to the description provided earlier in this application. The elements that are common and already described in reference with prior art FIG. 1 will not be described again in detail. Only the differences will be highlighted to illustrate the operation of the extended bandwidth SD-OCT system.

It may be noted that the signal processing function 1125 is shown as separate sub-unit in this figure. It may be part of a general digital signal processing (DSP) unit that also includes the FT unit 1118 and image generating unit 1119. Other variations of general DSP units with appropriate functionality incorporated in it are also included in this description. Similarly, the controller 1124 functions include but is not limited to, overall OCT system operation functions, signal processing, software and data storage, data manipulation, display (1120) and I/O capabilities. In general, the controller may be a computer including appropriate hardware and software functionalities to operate the OCT imaging system.

In operation, the controller 1124 activates the discrete source 1101 with a trigger signal 1121 and sends a signal to the detector readout matrix to convert the signals from the detector array elements 1116 into a time sequence of data which is a digital spectrum of the interference signal having the depth information for a given location of the sample under test. The bandwidth of the detector signal is the same as the source bandwidth. It was described earlier that the bandwidth can be further broadened by scaling up the magnitude of the weaker detected components that are around and somewhat beyond the band edges (defined by the half-power points in the spectrum). This process will preferentially increase the amplitude of the band edge elements relative to those at mid-band, thus advantageously provide further bandwidth enhancements at the system level beyond that which is already obtained by using the extended bandwidth broadband optical source described earlier in this application. Alternatively, the process would additionally modify the profile at other points in the spectrum (such as at mid-band) to convert it to a sideband-free Gaussian spectrum.

A preferred method for the post-detection bandwidth extension is to first determine the desired final profile $P_f$ for the output spectrum and multiply it term by term, with the detector signal profile $P_d$ using the data $P_m$ stored in the controller processor to compensate for the weak signal elements at the band edges of $P_d$ and provide any desired additional spectral modification. $P_f$ can be chosen to be Gaussian if the system's response after conversion to the time domain (an inverse Fourier transformation) is to be completely free of sidebands, or it can be a more or less flat spectrum if some amount of sideband (usually a few percents of the peak response) can be tolerated. Due to the discrete nature of the system, $P_f$ would also be a discrete set which would be the sum of individual components $P_{fi}$ where 'i' is the numerical order of detector elements.

The detected signal $P_d$, has individual elements $P_{th}$. An exemplary multiplier function $P_m$ is shown in FIG. 10(a), and its components $P_{mi}$ would be stored in the processor's memory. It would have the same number i of components as the detected signal components, and their values would be given by $P_{mi}=P_{fi}/P_{di}$. Then upon readout of the digital interference signal data, the software would sequentially read the detected signal component, fetch the corresponding multiplier element and perform the multiplications $P_{fi}=P_{di}*P_{mi}$ and feed the result to the Fourier transformation circuit 1118 or to a processor to implement the Fourier operation using a software tool.

In most of the discussion, the exemplary gain medium is chosen to be a waveguide SOA gain medium which comprise a doped semiconductor substrate which include but is not limited to, gallium arsenide, indium phosphide and others on which core and cladding waveguide layers are epitaxially deposited and processed using standard photolithography and etching processes well known in the art. The etalons, multilayer stacks, and gratings pertinent to this invention can be fabricated by standard thin film deposition techniques which are well known and well developed in the art of semiconductor device processing and thin film coatings.

A semiconductor chip may be the simplest choice for a gain medium due to its well known advantage such as small footprint, easy packaging with or without a thermoelectric cooler and temperature controller device, ease of coupling to an optical fiber, integration with other electronic components required for driver circuits and, signal processing etc. other gain medium such as optical amplifier structure, including rare-earth-doped silica fibers (erbium for 1,500-nm emission, praseodymium for 1,300-nm emission) and solid state laser structures, etc. are equally suitable for constructing extended bandwidth source according to the principles of this invention.

It may be recalled that the depth resolution of imaging is inversely proportional to the bandwidth. A combined effect of using an extended bandwidth light source and spectral correction outlined in this invention would result in better quality diagnostic images from a SD-OCT system configured according to the invention described in the disclosure. The concepts outlined here for extending bandwidth of optical imaging systems namely, feedback cavity design using reflectors that exhibit raised-edge reflectivity for providing bandwidth enhancement to a discrete spectrum optical sources, and performing post-detection digital signal processing are equally applicable to extend bandwidth of other gain media that may be known or occur to a person skilled in the art. While many possible combinations of constructing an extended bandwidth source may be apparent to those skilled in the art following the principles described in this application and explained using specific examples to illustrate the main concepts of the invention, the actual scope of the invention is presented in the following claims.

What is claimed is:

1. A broadband discrete spectrum optical source comprising:
   a gain medium having a wavelength dependent gain spectrum,
   a feedback cavity including at least two reflectors, wherein reflectivity of at least a first reflector is higher at wavelengths corresponding to the band edges than at midband of said gain spectrum, and wherein the reflectivity of the first reflector is substantially higher than the reflectivity of a second reflector; and
   the gain medium is disposed within the feedback cavity such that a light generated by adjusting the gain of the gain medium undergoes multiple reflections, thereby generating an output light having discrete emission lines with high output power over a bandwidth extended beyond the band edges of said gain spectrum.

2. The optical source as in claim 1, wherein the first and the second reflectors are, respectively, a back and a front reflector of the feedback cavity.

3. The optical source as in claim 1, wherein the first reflector is an etalon comprising a single layer of a dielectric material having a thickness equal to an odd multiple of one quarter wavelength of a preselected center wavelength.

4. The optical source as in claim 1, wherein the first reflector is an etalon comprising a stack of at least one pair of alternate layers of two different materials having a thickness equivalent of multiples of quarter wavelength and at least one pair of alternate layers of the same two materials having a thickness equivalent of multiples of half wavelengths, respectively, of a preselected center wavelength.

5. The optical source as in claim 1, wherein the first reflector is a double-pass grating.

6. The optical source as in claim 1, wherein the first reflector is disposed external to the gain medium at an adjustable distance, such that spatial distribution of the discrete emission lines of the source is altered by adjusting the distance between the first reflector and the gain medium.

7. The optical source as in claim 1, wherein the second reflector is directly disposed as an antireflection coating on one end facet of the gain medium.

8. The optical source as in claim 1, wherein the second reflector has wavelength dependent reflectivity, such that the reflectivity is higher at wavelengths corresponding to the band edges as compared to the reflectivity at wavelengths corresponding to the mid-band of said gain spectrum.

9. The optical source as in claim 8, wherein the second reflector comprises a single layer etalon having a thickness equal to an odd multiple of one quarter wavelength of a preselected center wavelength.

10. The optical source as in claim 8, wherein the second reflector is an etalon comprising a stack of at least one pair of alternate layers of two different materials having an equivalent thickness in multiples of quarter wavelength and at least one pair of alternate layers of the two materials, having an equivalent thickness in multiples of half wavelengths, and wherein said quarter and half wavelengths are in reference with a preselected center wavelength.

11. The optical source as in claim 1, wherein the gain medium comprises a super luminescent diode, a semiconductor optical amplifier or other semiconductor gain medium.

12. The optical source as in claim 11, wherein the gain medium includes a straight waveguide, a tilted waveguide, a bent waveguide or a curved waveguide.

13. The optical source as in claim 12, wherein the straight waveguide includes at least one perpendicular facet.

14. The optical source as in claim 13, wherein the second reflector is an etalon disposed on the at least one perpendicular facet, said etalon further including:
   at least two layers of different materials wherein refractive indexes and thickness of said layers are selected to have a combined refractive index and thickness equivalent to a quarterwave layer at a preselected center wavelength; and
   the combined refractive index of the etalon is substantially close but not equal to the geometric mean of the refractive indexes of the gain medium and a medium outside the feedback cavity, such that the etalon generates a raised edge reflectivity profile having a very low reflectivity near the mid-band of the gain medium spectrum.

15. The optical source as in claim 1, wherein the gain medium comprises an optical amplifier, an erbium doped fiber, a rare-earth-doped fiber, a solid state gain medium, or an amplified spontaneous emission source.

16. A broadband discrete spectrum optical source comprising:
- a gain medium, said gain medium further comprising a straight semiconductor waveguide with perpendicular end facets;
- a feedback cavity including;
    - a first reflector deposited on one end facet of the gain medium, said first reflector having a wavelength dependent reflectivity, such that the reflectivity at wavelengths corresponding to band edges is higher than the reflectivity at wavelengths corresponding to mid-band of the gain medium spectrum,
    - a second reflector deposited on a second end facet of the gain medium opposite from said first reflector, said second reflector having a reflectivity substantially lower than the reflectivity of the first reflector, said second reflector further comprising an etalon, wherein the etalon includes;
        - at least two layers of different materials wherein refractive indexes and thicknesses of said layers are selected to have a combined refractive index and thickness equivalent to a quarterwave layer at a preselected center wavelength;
        - the combined refractive index of the etalon is substantially close, but not equal to, the geometric mean of the refractive indexes of the gain medium and a medium outside the feedback cavity, such that the etalon generates a raised edge reflectivity profile having a very low reflectivity near the mid-band of the gain medium spectrum; and
        - the gain medium is disposed within the feedback cavity such that a light generated by adjusting the gain of the gain medium undergoes multiple reflections between the first and second reflectors, thereby generating a discrete spectrum optical output having a high-output power over a bandwidth extended beyond the band edges of said gain medium spectrum.

17. The optical source as in claim 16, wherein the first reflector comprises a single layer etalon with a thickness equal to an odd multiple of one quarter wavelength of a preselected center wavelength.

18. The optical source as in claim 16, wherein the first reflector is an etalon comprising a stack of at least one pair of alternate layers of two different materials having a thickness equivalent of multiples of quarter wavelengths and at least one pair of alternate layers of the same two materials having a thickness equivalent of multiples of half wavelengths, respectively, of a preselected center wavelength.

19. The optical source as in claim 16, wherein the first reflector is a double-pass grating.

20. An optical imaging system comprising:
- a discrete spectrum light source;
- an interferometer including a reference arm and a sensing arm, wherein optical power directed in the sensing arm is substantially smaller than the optical power directed in the reference arm;
- a dispersive device to separate different wavelength components of an interference signal generated in the interferometer;
- a detector array including a plurality of detectors to detect different wavelength components of the interference signal, such that the detector array simultaneously detects all the wavelength components of the interference signal sequentially, and generates a digital spectrum of the interference signal; and
- a processor for applying a correction to each detected signal by a respective predetermined amount according to a prescribed correction signal, said correction signal having a wavelength dependent spectral profile, such that the correction applied to the interference signal detected near the band edges is higher than at the mid-band of the interference signal, so that the corrected spectrum of the imaging system has a predetermined spectral profile and a higher bandwidth as compared to the bandwidth of the discrete spectrum light source.

21. The optical imaging system as in claim 20, wherein the discrete spectrum light source further includes:
- a feedback cavity having at least two reflectors, wherein a reflectivity of a first reflector is substantially higher than the reflectivity of a second reflector, and wherein the second reflector functions as an output port; and
- a gain medium placed within the feedback cavity such that a light generated by adjusting the gain of the gain medium undergoes multiple reflections between the first and second reflectors, thereby generating an output light having a discrete set of emission lines having high peak power.

22. The optical imaging system as in claim 21, wherein the reflectivity of the first and second reflectors are wavelength dependent, such that the reflectivity at wavelengths corresponding to the band edges is higher than reflectivity at wavelengths corresponding to the mid-band of the gain medium spectrum, thereby extending the bandwidth of the discrete spectrum light source beyond the band edges of the gain medium spectrum resulting in higher resolution of the optical imaging system.

23. The optical imaging system as in claim 21, wherein the first reflector is disposed external to the gain medium at an adjustable distance, whereupon by adjusting the distance between the first reflector and the gain medium, spatial distribution of the discrete emission lines of the source is varied to match the spatial distribution of the detectors in the detector array.

24. The imaging system as in claim 20, wherein the wavelength dependent spectral profile of the correction signal is determined according to a predetermined final bandwidth and spectral profile required for the detected interference signal, such that the processor applies the correction signal to the detected signal at each wavelength, respectively, in a predetermined mathematical operation.

* * * * *